(12) United States Patent
Yui et al.

(10) Patent No.: US 6,483,120 B1
(45) Date of Patent: Nov. 19, 2002

(54) CONTROL SYSTEM FOR A CHARGED PARTICLE EXPOSURE APPARATUS

(75) Inventors: Yoshikiyo Yui, Utsunomiya (JP); Masato Muraki, Inagi (JP)

(73) Assignee: Canon Kabushiki Kaisha, Tokyo (JP)

( * ) Notice: Subject to any disclaimer, the term of this patent is extended or adjusted under 35 U.S.C. 154(b) by 0 days.

(21) Appl. No.: 09/639,078

(22) Filed: Aug. 16, 2000

(30) Foreign Application Priority Data

Aug. 31, 1999 (JP) .......................................... 11-246727

(51) Int. Cl.$^7$ .......................... G01N 23/00; A61N 5/00; G06E 17/50
(52) U.S. Cl. ................ 250/491.1; 250/492.2; 250/492.22; 716/21; 716/8; 716/9
(58) Field of Search ................................. 250/310, 311, 250/398, 492.2, 492.22, 491.1; 716/8, 21, 9, 19

(56) References Cited

U.S. PATENT DOCUMENTS

| | | | |
|---|---|---|---|
| 4,794,646 A | * 12/1988 | Takeuchi et al. | 382/8 |
| 5,428,552 A | * 6/1995 | Rudert et al. | 250/398 |
| 5,578,821 A | * 11/1996 | Meisberger et al. | 250/310 |
| 5,699,266 A | * 12/1997 | Chung et al. | 250/492.22 |
| 5,834,783 A | 11/1998 | Muraki et al. | 250/398 |
| 5,973,332 A | 10/1999 | Muraki et al. | 250/492.2 |
| 6,353,922 B1 | * 3/2002 | Dick | 250/491.1 |

* cited by examiner

*Primary Examiner*—John R. Lee
*Assistant Examiner*—Kalimah Fernandez
(74) *Attorney, Agent, or Firm*—Fitzpatrick, Cella, Harper & Scinto

(57) ABSTRACT

A control system is provided for a charged particle exposure apparatus. A plurality of dot control data are concatenated and compressed to generate compressed concatenated control data. A plurality of compressed concatenated control data are arranged to generate exposure control data. An electron beam exposure apparatus expands the exposure control data to reconstruct the plurality of dot control data, and performs exposure while controlling blankers on the basis of the reconstructed dot control data.

27 Claims, 20 Drawing Sheets

| 1 | 1 | 1 | 1 | 0 | 0 | 0 | 0 |
| 1 | 1 | 1 | 1 | 1 | 1 | 1 | 1 |
| 0 | 0 | 0 | 0 | 1 | 1 | 1 | 1 |
| 1 | 1 | 1 | 1 | 1 | 1 | 1 | 1 |

CONCATENATED CONTROL DATA BEFORE COMPRESSION

CONTROL SYSTEM FOR A CHARGED PARTICLE EXPOSURE APPARATUS

FIELD OF THE INVENTION

The present invention relates to a charged particle exposure apparatus and a control method therefor and, more particularly, to a charted particle exposure apparatus having a plurality of control elements for controlling operation of drawing a pattern on a substrate with a charged particle beam and a control method therefor, an information processing apparatus for generating exposure control data to be supplied to the charged particle exposure apparatus and a control method therefor, and a device manufacturing method using a charged particle exposure apparatus controlled by this control method.

BACKGROUND OF THE INVENTION

Examples of a charged particle exposure apparatus are an electron beam exposure apparatus and an ion beam exposure apparatus. The charged particle exposure apparatus is used for drawing a desired pattern on a substrate (e.g., a wafer or glass plate) for forming, e.g., a semiconductor integrated circuit, a mask or reticle used for manufacturing a semiconductor integrated circuit, or a display device such as an LCD.

The charged particle exposure apparatus scans a substrate with a charged particle beam while turning on/off a blanker that controls irradiation of the charged particle beam, thereby drawing a desired pattern on a resist on the substrate. Accordingly, the charged particle exposure apparatus requires a very large amount of exposure control data for controlling exposure performed by the charged particle beam.

FIG. 20 is a block diagram showing the schematic arrangement of a conventional charged particle exposure apparatus. For example, a storage 1101 is comprised of a hard disk device, and stores exposure control data for controlling exposure. The exposure control data is compressed and stored in the storage 1101 in order to reduce the data size. In exposure, necessary portions of a series of exposure control data are sequentially read out from the storage 1101 and are temporarily stored in a buffer memory 1102.

An expansion processor 1103 develops (expands) partial exposure control data temporarily stored in the buffer memory 1102, and supplies them to a correction processor 1104. The correction processor 1104 performs correction for decreasing the influence of a proximity effect, or corrects drift of the charged particle beam, and supplies corrected data to drivers 1105 to 1107.

A main body 1110 of the exposure apparatus has a blanker 1111 for controlling irradiation of the charged particle beam, a deflector 1112 for deflecting the charged particle beam, and a correction coil 1113 for correcting the focal position or aberration, all of which are driven by the drivers 1105 to 1107, respectively.

As described above, in general, the exposure control data are stored in the storage 1101 in the compressed state in order to decrease the data size. Even compressed, the data amount of the exposure control data is very large.

Therefore, a method of efficiently compressing exposure control data to be supplied to a charged particle exposure apparatus, without increasing the load of the charged particle exposure apparatus which uses the compressed exposure control data by expansion, is sought for.

SUMMARY OF THE INVENTION

The present invention has been made in view of the above situation, and has as its object to for example decrease the load of processing of a charged particle exposure apparatus when expanding exposure control data.

It is another object of the present invention to reduce the data size of exposure control data to be supplied to, e.g., a charged particle exposure apparatus.

According to the first aspect of the present invention, there is provided a charged particle exposure apparatus having a plurality of control elements for controlling operation of drawing a pattern on a substrate with a charged particle beam, comprising a storage for storing exposure control data including concatenated control data generated by concatenating and thereafter compressing at least two control data for respectively controlling at least two of the plurality of control elements within the same period, and a processor for reconstructing at least two control data by expanding the concatenated control data included in the exposure control data stored in the storage, and controlling at least two control elements in accordance with the two control data.

In the charged particle exposure apparatus according to the first aspect of the present invention, for example, the exposure control data preferably includes a plurality of concatenated control data arranged in an order with which they are used for control.

In the charged particle exposure apparatus according to the first aspect of the present invention, for example, at least two control elements are preferably control elements of the same type.

In the charged particle exposure apparatus according to the first aspect of the present invention, for example, the apparatus preferably further comprises a charged particle source for generating a plurality of charged particle beams, and the plurality of control elements preferably include a plurality of irradiation controllers for separately controlling whether the substrate is to be irradiated with the plurality of charged particle beams.

In the charged particle exposure apparatus according to the first aspect of the present invention, for example, each of the irradiation controllers preferably includes a blanker for controlling whether the charged particle beam is to be deflected.

In the charged particle exposure apparatus according to the first aspect of the present invention, for example, the exposure control data preferably includes a plurality of concatenated control data, and each of the concatenated control data is preferably generated by concatenating and compressing at least two control data for respectively controlling at least two adjacent ones of the irradiation controllers.

In the charged particle exposure apparatus according to the first aspect of the present invention, for example, the control data for controlling the irradiation controllers are preferably time series data generated by arranging information, indicating whether the charged particle beams are to irradiate, in an order with which they are used for control.

In the charged particle exposure apparatus according to the first aspect of the present invention, for example, the concatenated control data is preferably generated by concatenating in series and compressing at least two of the control data serving as time series data.

In the charged particle exposure apparatus according to the first aspect of the present invention, for example, the concatenated control data is preferably generated by concatenating in parallel and compressing at least two of the control data serving as time series data.

In the charged particle exposure apparatus according to the first aspect of the present invention, for example, the plurality of control elements preferably include an irradiation controller for controlling whether the substrate is to be irradiated with the charged particle beam, a deflector for scanning the substrate with the charged particle beam, and a focus controller for controlling focus, and the concatenated control data is preferably generated by concatenating and compressing at least two of control data for controlling the irradiation controller, control data for controlling the deflector, and control data for controlling the focus controller.

In the charged particle exposure apparatus according to the first aspect of the present invention, for example, the apparatus preferably further comprises a data generator for generating the exposure control data on the basis of a pattern to be drawn on the substrate.

According to the second aspect of the present invention, there is provided a method of controlling a charged particle exposure apparatus having a plurality of control elements for controlling operation of drawing a pattern on a substrate with a charged particle beam, the method comprising the steps of reading out, from a storage, exposure control data including concatenated control data generated by concatenating and thereafter compressing at least two control data for respectively controlling at least two of the plurality of control elements within the same period, expanding the concatenated control data included in the read exposure control data, thereby reconstructing the at least two control data, and controlling the at least two control elements in accordance with the at least two control data reconstructed in the expanding step.

According to the third aspect of the present invention, there is provided an information processing apparatus for generating exposure control data to be supplied to a charged particle exposure apparatus having a plurality of control elements for drawing a pattern on a substrate with a charged particle beam, comprising a first data generator for generating concatenated control data by concatenating and compressing at least two control data for respectively controlling at least two of the plurality of control elements within the same period, and a second data generator for generating exposure control data including the concatenated control data.

According to the fourth aspect of the present invention, there is provided an information processing method of generating exposure control data to be supplied to a charged particle exposure apparatus having a plurality of control elements for drawing a pattern on a substrate with a charged particle beam, comprising the first data generating step of generating concatenated control data by concatenating and compressing at least two control data for respectively controlling at least two of the plurality of control elements within the same period, and the second data generating step of generating exposure control data including the concatenated control data.

According to the fifth aspect of the present invention, there is provided a memory medium for storing a control program that generates exposure control data to be supplied to a charged particle exposure apparatus having a plurality of control elements for drawing a pattern on a substrate with a charged particle beam, the control program including the first data generating step of generating concatenated control data by concatenating and compressing at least two control data for respectively controlling at least two of the plurality of control elements within the same period, and the second data generating step of generating exposure control data including the concatenated control data.

According to the sixth aspect of the present invention, there is provided a device manufacturing method comprising the step of drawing a pattern on a substrate while controlling a charged particle exposure apparatus in accordance with a control method according to the second aspect described above.

According to the seventh aspect of the present invention, there is provided a device manufacturing method using, in some of steps thereof, a charged particle exposure apparatus having a plurality of control elements for controlling operation of drawing a pattern on a substrate with a charged particle beam, the method serving to perform, with the charged particle exposure apparatus, the steps of reading out, from a storage, exposure control data including concatenated control data generated by concatenating and thereafter compressing at least two control data for respectively controlling at least two of the plurality of control elements within the same period, expanding the concatenated control data included in the read exposure control data, thereby reconstructing at least two control data, and drawing a pattern on the substrate while controlling at least two control elements and other control elements in accordance with at least two reconstructed control data and other control data.

Other features and advantages of the present invention will be apparent from the following description taken in conjunction with the accompanying drawings, in which like reference characters designate the same or similar parts throughout the figures thereof.

BRIEF DESCRIPTION OF THE DRAWINGS

The accompanying drawings, which are incorporated in and constitute a part of the specification, illustrate embodiments of the invention and, together with the description, serve to explain the principles of the invention.

FIG. 13 shows another example of how to concatenate control data (i.e., dot control data) that control ON/OFF of the electron beam by the blanker;

DETAILED DESCRIPTION OF THE PREFERRED EMBODIMENTS

An electron beam exposure apparatus will be described as an example of a charged particle exposure apparatus. Note that the present invention can be applied not only to the electron beam exposure apparatus but also to, e.g., an ion beam exposure apparatus.

Figure 1:
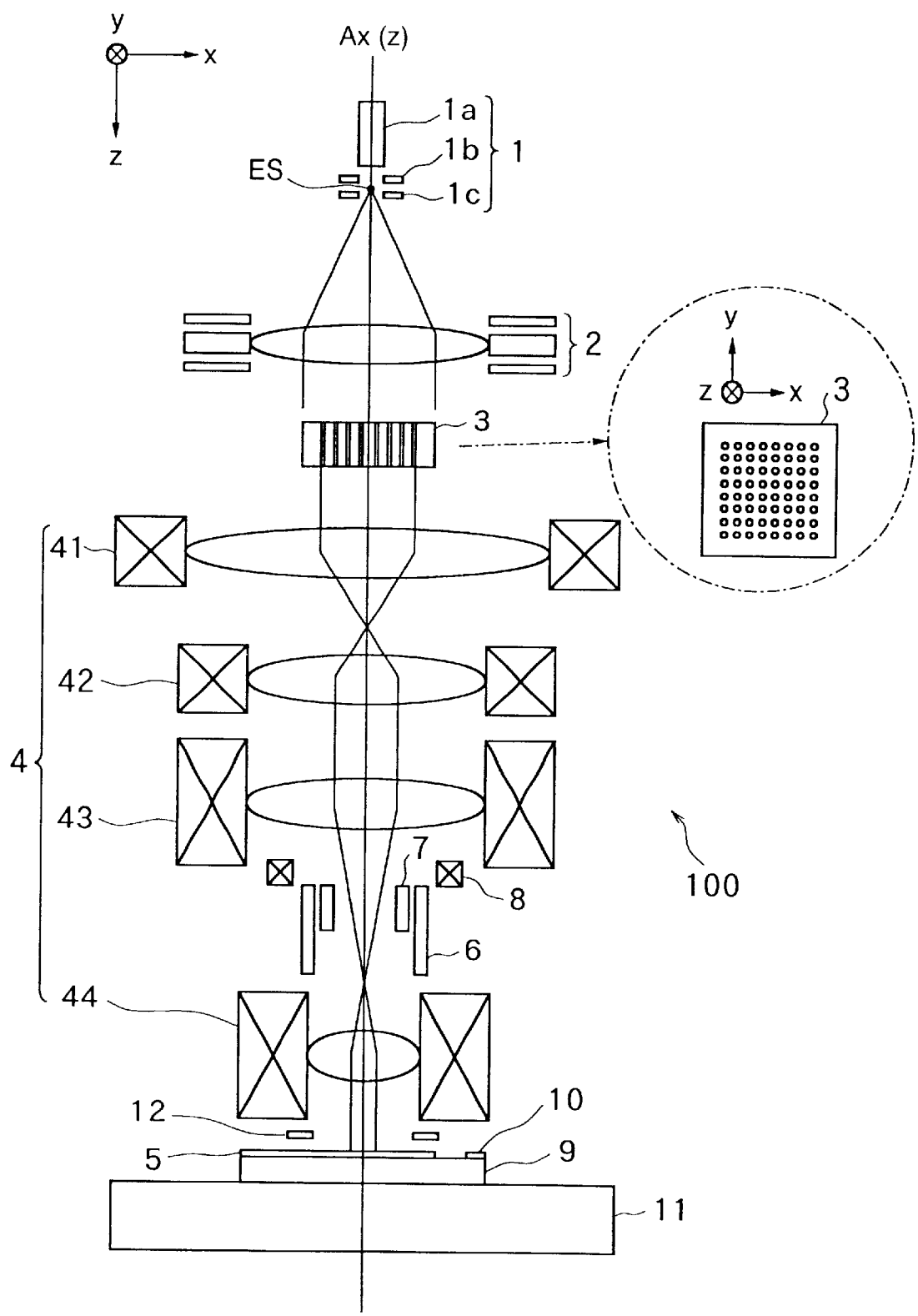
FIG. 1 is a schematic view of an electron beam exposure apparatus according to a preferable embodiment of the present invention.

FIG. 1 is a schematic view of an electron beam exposure apparatus according to one preferred embodiment of the present invention. Referring to FIG. 1, reference numeral 1 denotes an electron gun including a cathode 1a, grid 1b, and anode 1c. Electrons emitted by the cathode 1a form a cross-over image as an electron source ES between the grid 1b and anode 1c.

The electrons emitted from the electron source ES irradiate an element electron optical system array 3 through a condenser lens 2. The condenser lens 2 is made up of, e.g., three aperture electrodes.

Figure 2A:
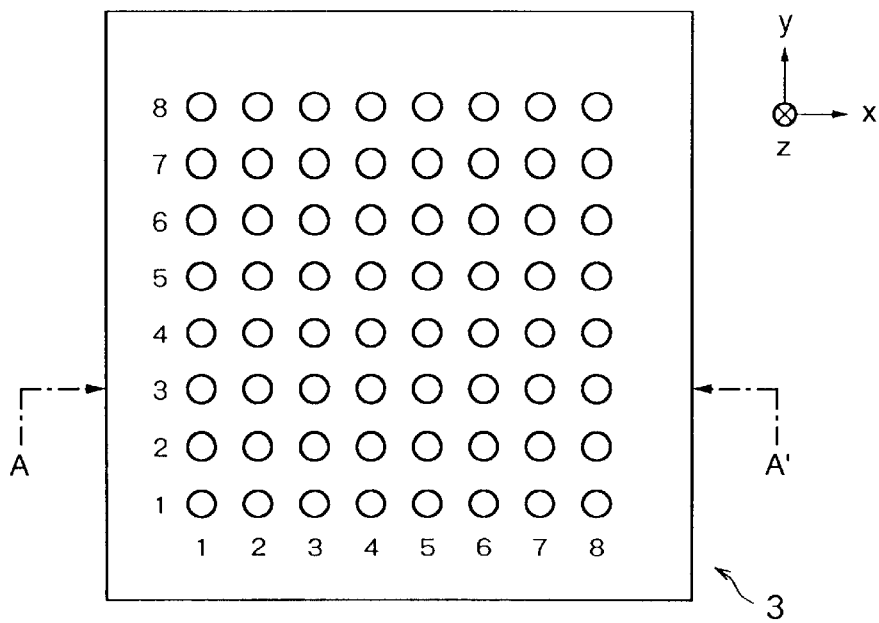
FIGS. 2A and 2B are views showing the arrangement of an element electron optical system array in detail.
Figure 2B:
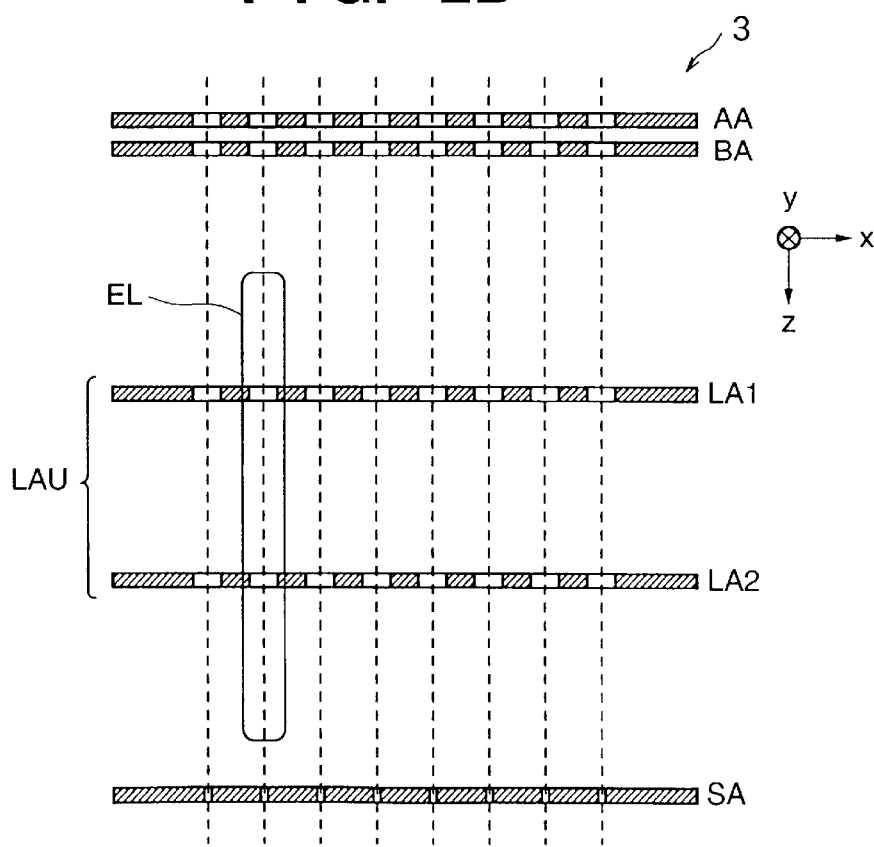

As shown in FIG. 2B, the element electron optical system array 3 is comprised of an aperture array AA, blanker array BA, element electron optical system array unit LAU, and stopper array SA sequentially arranged from the electron gun 1 side along an optical axis AX. The element electron optical system array 3 will be described in detail later.

The element electron optical system array 3 forms a plurality of intermediate images of the electron source ES, and the respective intermediate images are reduced and projected by a reduction electron optical system 4 (to be described later) onto a substrate 5 such as a wafer. Accordingly, a plurality of electron source images having the same shape are formed on the substrate 5. The element electron optical system array 3 forms the plurality of intermediate images so as to correct aberration that occurs when the plurality of intermediate images are reduced and projected onto the substrate 5 through the reduction electron optical system 4.

The reduction electron optical system 4 is comprised of a symmetric magnetic doublet constituted by first and second projection lenses 41 and 42 and a symmetric magnetic doublet constituted by first and second projection lenses 43 and 44. Assuming that the focal length of the first projection lens 41 (43) is f1 and that of the second projection lens 42 (44) is f2, the distance between these two lenses is f1+f2.

The object point on the optical axis AX is located at the focal position of the first projection lens 41 (43), and its image point is formed on the focal point of the second projection lens 42 (44). This image is reduced to −f2/f1 the original size. In this exposure apparatus 100, two lens magnetic fields are determined to act in opposite directions. Hence, theoretically, Seidel aberrations excluding spherical aberration, isotropic astigmatism, isotropic coma, curvature of field, and on-axis chromatic aberration, and chromatic aberrations concerning rotation and magnification are canceled.

Reference numeral 6 denotes a deflector for deflecting a plurality of electron beams from the element electron optical system array 3 to displace the plurality of electron source images on the substrate 5 in the X and Y directions by substantially the same displacement amounts. Although not shown, the deflector 6 is comprised of a main deflector used when the deflection width is large, and a subdeflector used when the deflection width is small. The main deflector is an electromagnetic deflector, and the subdeflector is an electrostatic deflector.

Reference numeral 7 denotes a dynamic focus coil for correcting an error in focal position of the electron source image produced by a deflection aberration which occurs when the deflector 6 is operated. Reference numeral 8 denotes a dynamic stigmatic coil for correcting astigmatism of the deflection aberration caused by deflection.

Reference numeral 9 denotes a θ-Z stage movable in the direction of the optical axis AX (Z-axis) and a rotational direction about the Z-axis. A stage reference plate 10 is fixed to the θ-Z stage 9.

Reference numeral 11 denotes an X-Y stage on which the θ-Z stage 9 is placed and which is movable in the X and Y directions perpendicular to the optical axis AX (Z-axis).

Reference numeral 12 denotes a reflected electron detector for detecting reflected electrons produced when a mark on the stage reference plate 10 is irradiated with the electron beam.

The arrangement of the element electron optical system array 3 will be described with reference to FIGS. 2A and 2B. As described above, the element electron optical system array 3 is comprised of the aperture array AA, blanker array BA, element electron optical system array unit LAU, and stopper array SA. FIG. 2A is a view of the element electron optical system array 3 seen from the electron gun 1 side, and FIG. 2B is a sectional view taken along the line A–A' of FIG. 2A.

The aperture array AA is comprised of a board having a plurality of openings, as shown in FIG. 2A, to divide the electron beam from the condenser lens 2 into a plurality of electron beams.

Figure 3:
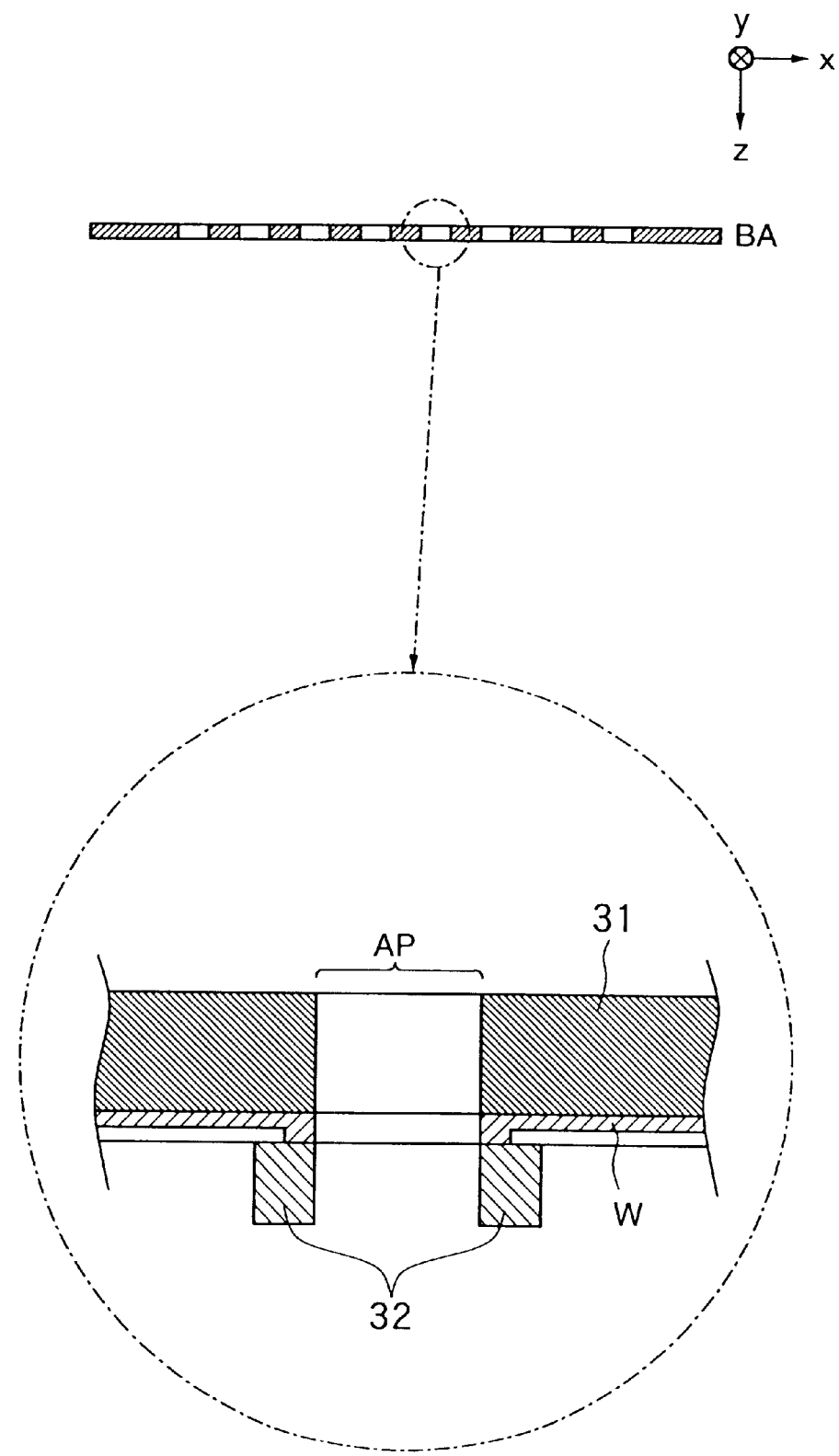
FIG. 3 is a view showing one deflector among those formed in a blanker array.
Figure 4:
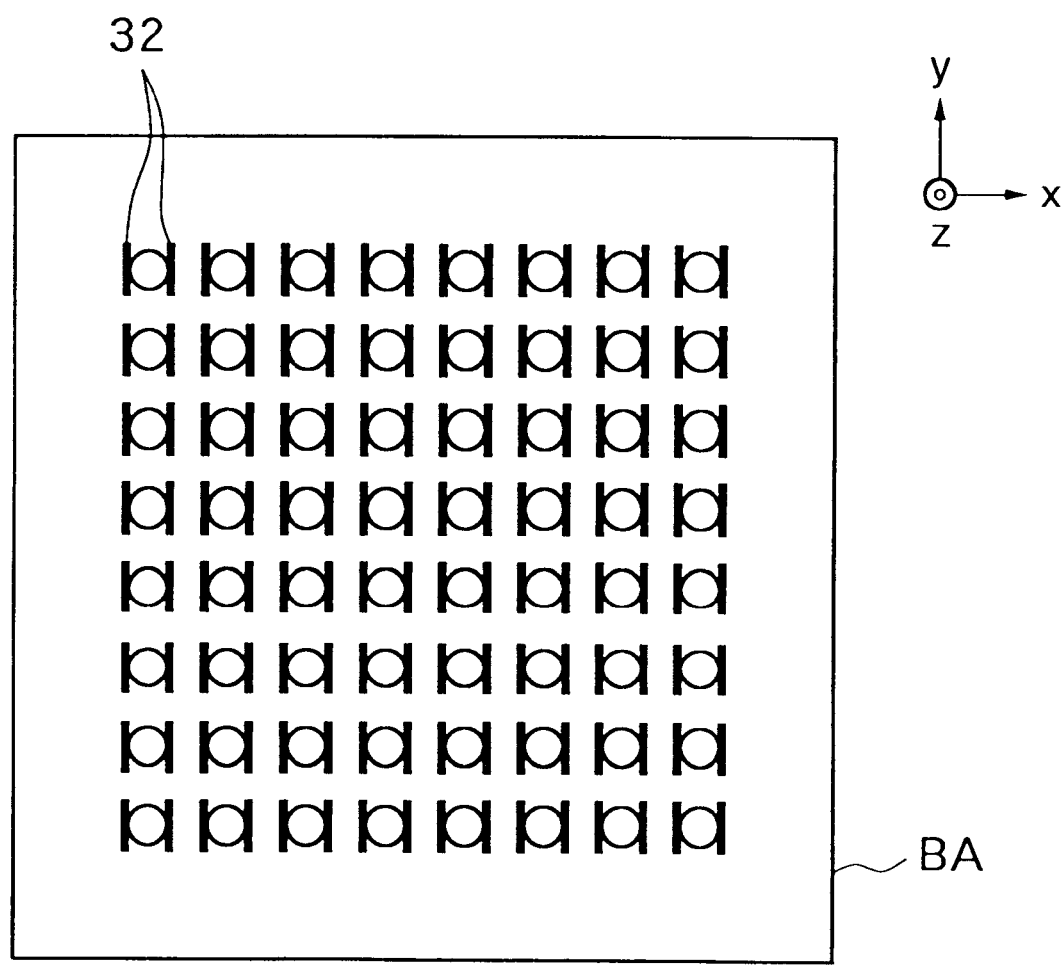
FIG. 4 is a bottom view of the blanker array.

The blanker array BA is obtained by forming a plurality of deflectors, that individually deflect the respective electron beams formed by the aperture array AA, on one board. FIG. 3 is a view showing one deflector among those formed on the blanker array BA. The blanker array BA is comprised of a board 31 having a plurality of openings AP, blankers 32 each formed of a pair of electrodes sandwiching one opening AP and having a deflecting function, and wiring lines W for turning on/off the blankers 32 separately. FIG. 4 is a bottom view of the blanker array BA.

The element electron optical system array unit LAU is comprised of first and second electron optical system arrays LA1 and LA2 each of which is an electron lens array formed by aligning a plurality of electron lenses two-dimensionally within one plane.

Figure 5:
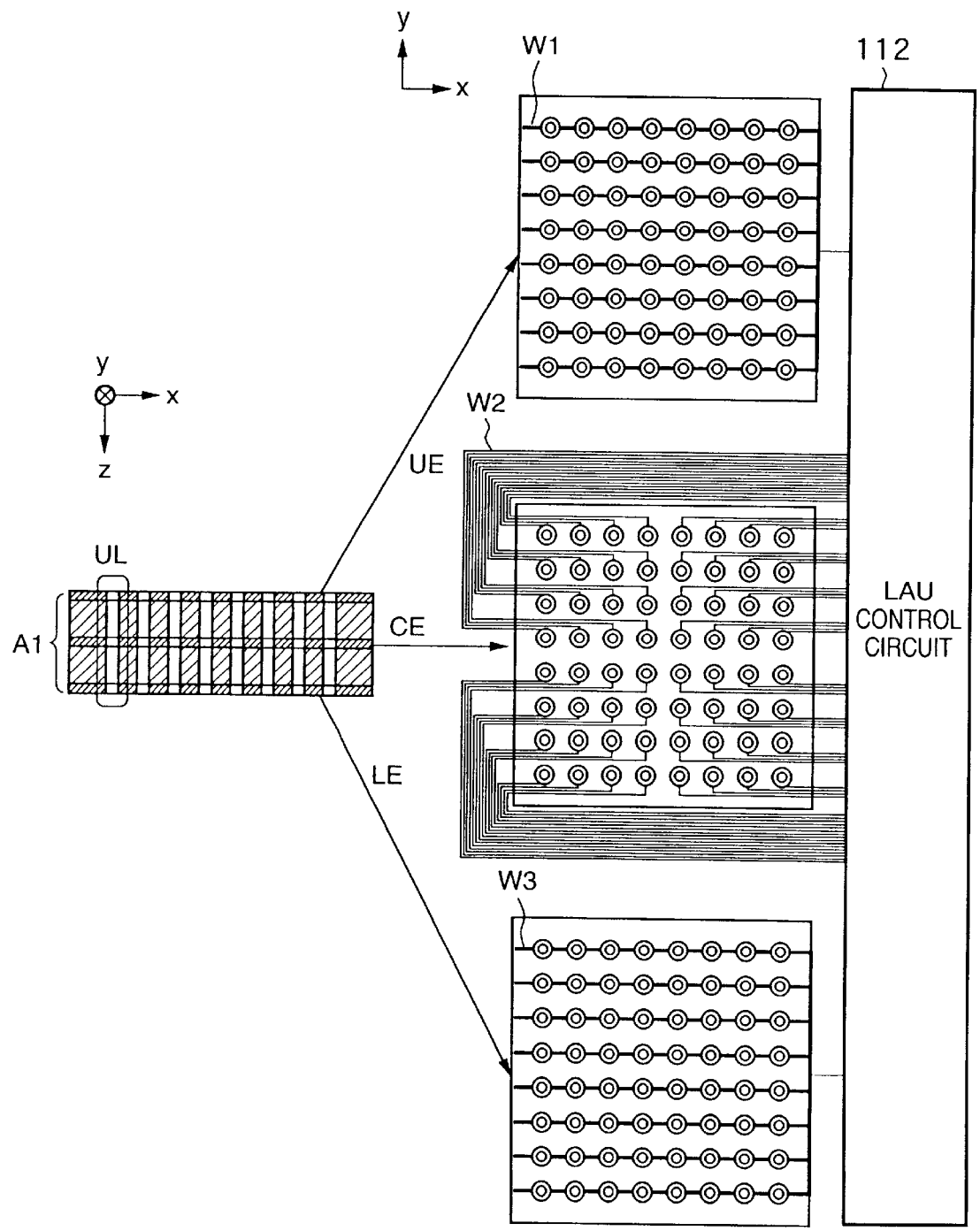
FIG. 5 is a view for explaining first and second electron optical system arrays.

FIG. 5 is a view for explaining the first electron optical system array LA1. The first electron lens array LA1 has an upper electrode plate UE, intermediate electrode plate CE, and lower electrode plate LE each having a plurality of rows of annular electrodes corresponding to the plurality of openings. These three electrode plates are overlaid on each other through insulators.

The annular electrodes with the same X- and Y-coordinates on the upper, intermediate, and lower electrode plates UE, CE, and LE constitute one electron lens (a so-called unipotential lens) UL. The annular electrodes on the upper electrode plate UE of the respective electron lenses UL are connected to an LAU control circuit 112 through common wiring lines W1, and the annular electrodes on the lower electrode plate LE of the respective electron lenses UL are connected to the LAU control circuit 112 through common wiring lines W3. A potential for accelerating the electron beams is applied across the annular electrodes on the upper and lower electrode plates UE and LE. An appropriate potential is applied to the annular electrodes on the intermediate electrode plate CE of the respective electron lenses from the LAU control circuit 112 through separate wiring lines W2. Thus, the electron optical power (focal length) of each electron lens can be set to a desired value.

The second electron optical system array LA2 has the same structure and function as those of the first electron optical system array LA1.

As shown in FIG. 2B, in the element electron optical system array unit LAU, the electron lenses of the first and second electron optical system arrays LA1 and LA2 with the same X- and Y-coordinates constitute one element electron optical system EL.

The aperture array AA is located at substantially the front focal positions of the respective element electron optical systems EL. Each element electron optical system EL forms an intermediate image of the electron source ES at substantially its rear focal position with the divided electron beam. The potential to be applied to the annular electrodes on the intermediate electrode plate CE is adjusted in units of element electron optical systems EL, such that the curvature of field produced when the intermediate image is reduced and projected onto the substrate 5 through the reduction electron optical system 4 is corrected. Thus, the electron optical power of the electron lens is adjusted, and the position where the intermediate image is to be formed is adjusted.

Similarly to the aperture array AA, the stopper array SA is comprised of a board having a plurality of openings. Electron beams deflected by the blanker array BA irradiate portions of the stopper array SA that are outside the openings and correspond to the electron beams, and are blocked by the board.

Figure 6:
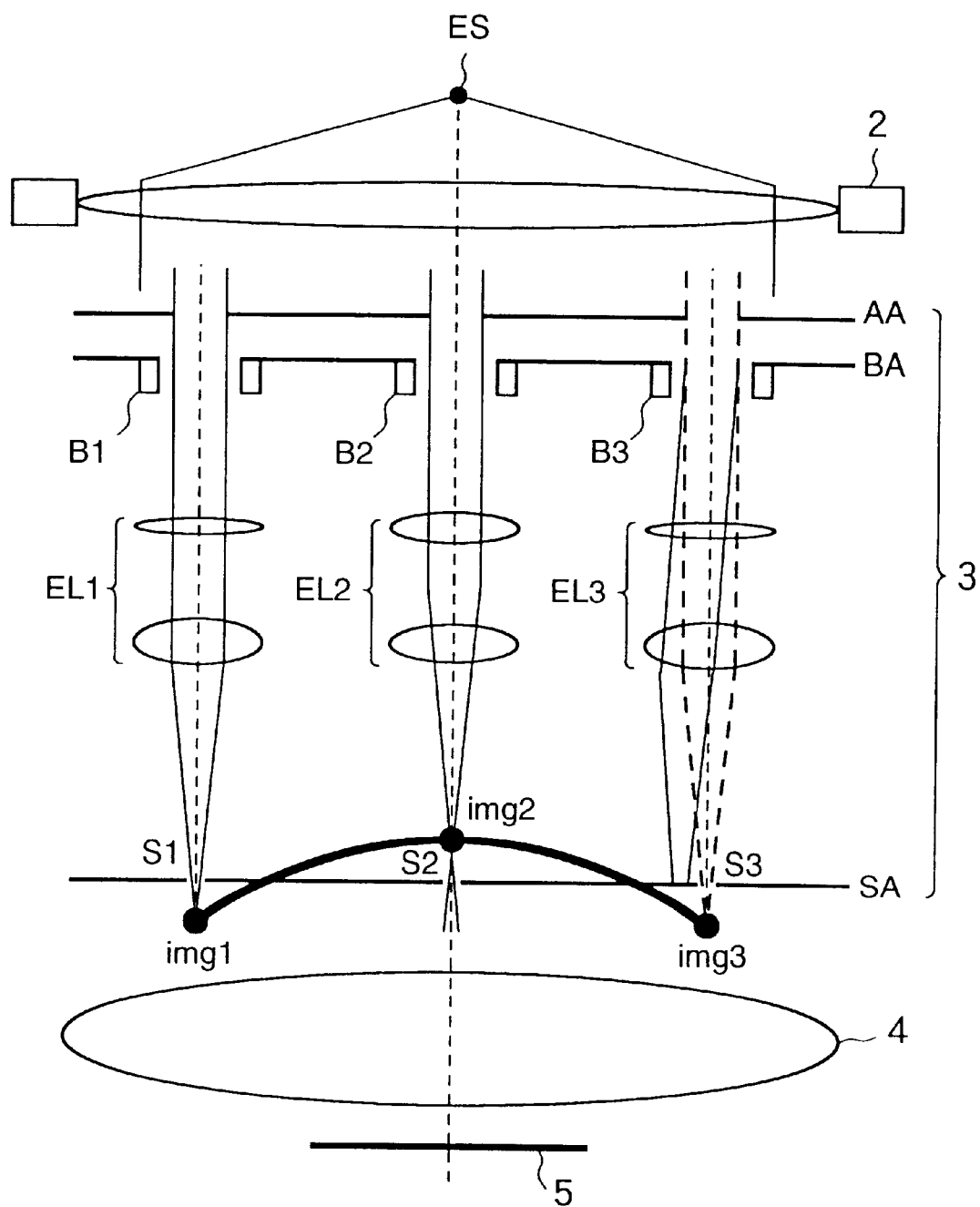
FIG. 6 is a view for explaining the function of the element electron optical system array.

The function of the element electron optical system array 3 will be described with reference to FIG. 6. The electrons emitted by the electron source ES pass through the condenser lens 2 to form substantially parallel electron beams. The substantially parallel electron beams are divided into a plurality of electron beams by the aperture array AA with the plurality of openings. The divided electron beams respectively come incident on element electron optical systems EL1 to EL3 to form intermediate images img1 to img3 of the electron source ES at the substantially front focal positions of the respective element electron optical systems EL1 to EL3. The respective intermediate images img1 to img3 are projected onto the substrate 5 as the exposure target surface through the reduction electron optical system 4.

In order to correct the curvature of field (en error between the actual image-forming position on the substrate 5 and the ideal image-forming position in the direction of optical axis of the reduction electron optical system 4) which occurs when the plurality of intermediate images are projected onto the exposure target surface, the optical characteristics of the plurality of element electron optical systems are set separately, so that the positions in the direction of optical axis where the intermediate images are to be formed differ from one element electron optical system to another.

Blankers B1 to B3 of the blanker array AA and stoppers S1 to S3 of the stopper array SA individually control whether or not the substrate 5 is to be irradiated with the respective electron beams. In FIG. 6, since the blanker B3 is ON, the electron beam for forming the intermediate image img3 does not pass through the opening S3 of the stopper array SA but is blocked by the board of the stopper array SA.

Figure 7:
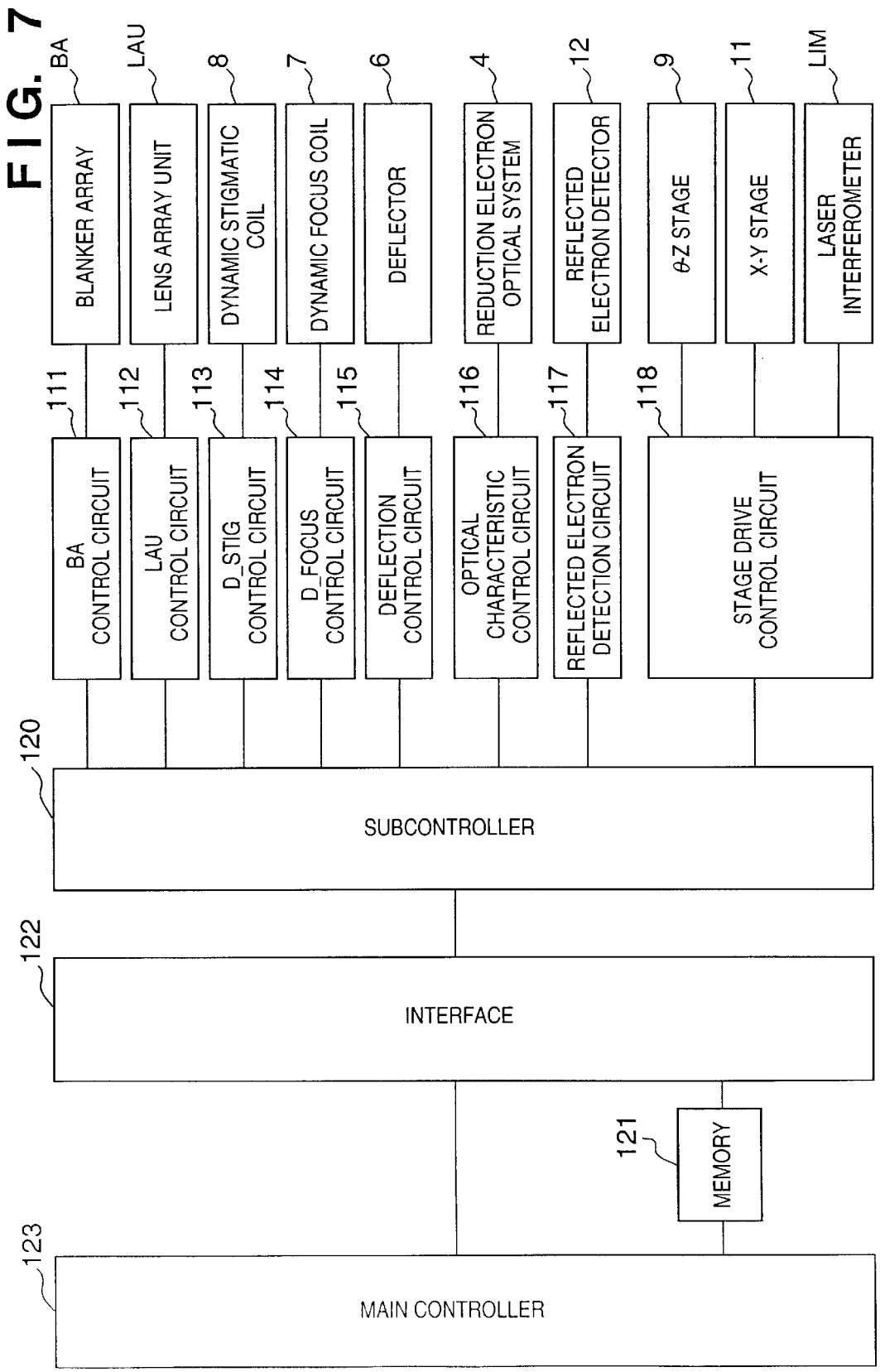
FIG. 7 is a block diagram showing the arrangement of the control system of the electron beam exposure apparatus shown in FIG. 1.

FIG. 7 is a block diagram showing the arrangement of the control system of the electron beam exposure apparatus 100 shown in FIG. 1. A BA control circuit 111 individually controls ON/OFF of the respective bankers of the blanker array BA. An LAU control circuit 112 controls the focal length of the electron lenses EL constituting the lens array unit LAU. A D_STIG control circuit 113 controls the dynamic stigmatic coil 8 to correct the astigmatism of the reduction electron optical system 4. A D_focus control circuit 114 controls the dynamic focus coil 7 to adjust the focus of the reduction electron optical system 4. A deflection control circuit 115 controls the deflector 6. An optical characteristic control circuit 116 adjusts the optical characteristics (magnification, distortion) of the reduction electron optical system 4. A reflected electron detection circuit 117 calculates the amount of reflected electrons from a signal sent from the reflected electron detector 12.

A stage drive control circuit 118 drive-controls the θ-Z stage 9 and, in cooperation with a laser interferometer LIM that detects the position of the X-Y stage 11, the X-Y stage 11.

A subcontroller 120 reads out exposure control data stored in a memory 121 through an interface 122, and controls the control circuits 111 to 116 and 118 and the reflected electron detection circuit 117 on the basis of the read result. A main controller 123 controls the whole electron beam exposure apparatus 100 in a general manner.

The schematic operation of the electron beam exposure apparatus 100 shown in FIG. 1 will be described with reference to FIG. 7.

The subcontroller 120 reads out the compressed exposure control data from the memory 121 and expands it. The subcontroller 120 extracts deflection control data (reference position of the main deflector and reference position of the subdeflector) as control data for controlling the deflector 6 from the expanded exposure control data, and supplies it to the deflection control circuit 115. The subcontroller 120 also sequentially extracts blanker control data (e.g., dot control data or dose control data) as control data for controlling the blankers of the blanker array BA from the expanded exposure control data, and supplies them to the BA control circuit 111.

The deflection control circuit 115 controls the deflector 6 on the basis of the deflection control data to deflect a plurality of electron beams. Simultaneously to this, the BA control circuit 111 controls the blankers of the blanker array BA and turns them on/off in accordance with a pattern to be drawn on the substrate 5. When the substrate 5 is to be scanned by a plurality of electron beams to draw a pattern on the substrate 5, the X-Y stage 11 is continuously driven in the Y direction, and the plurality of electron beams are deflected by the deflector 6 to follow the movement of the X-Y stage 11.

Figure 8:
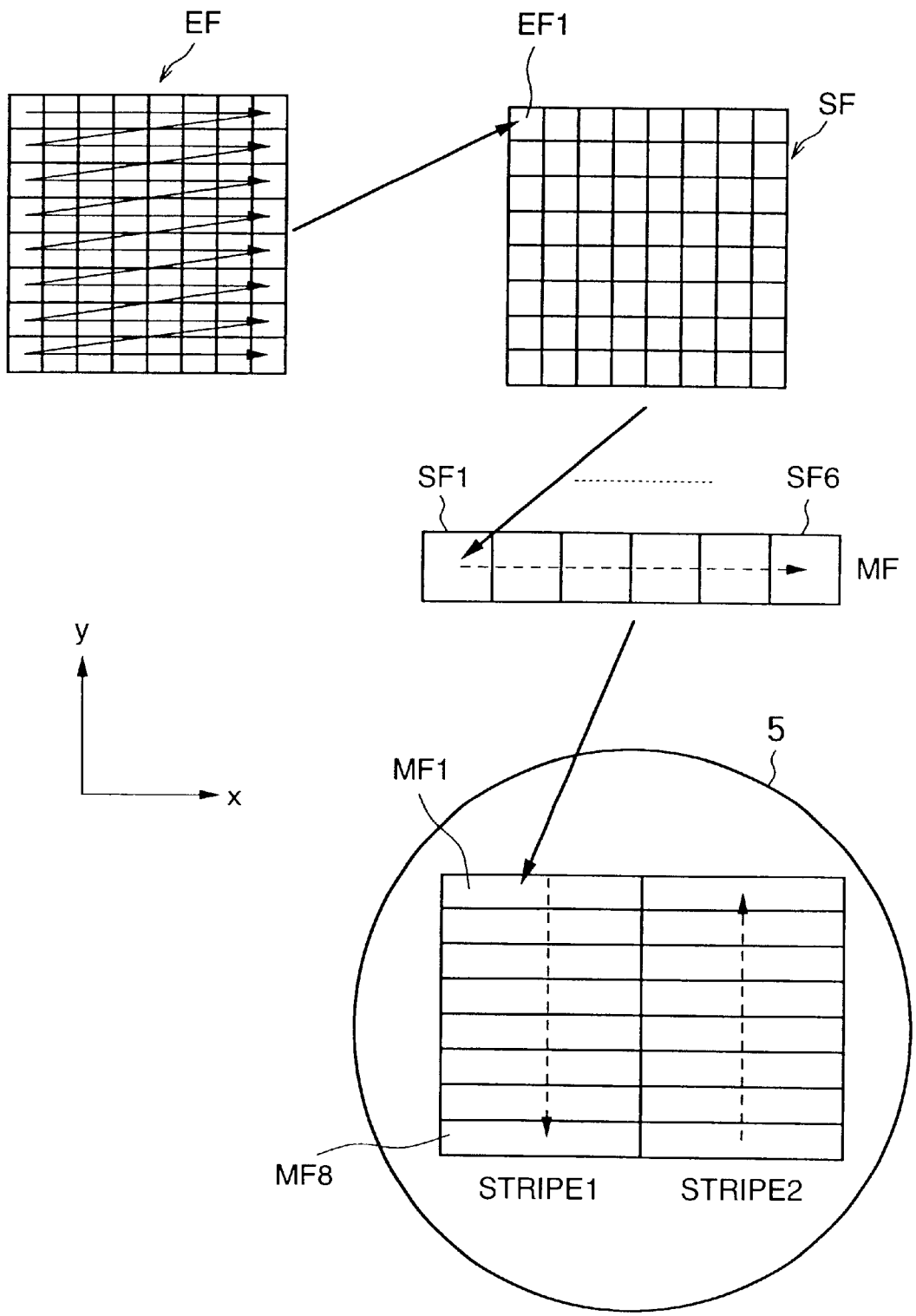
FIG. 8 includes views for explaining the principle of exposure performed by the electron beam exposure apparatus shown in FIG. 1.

The electron beams scan and expose the corresponding element exposure regions (EF) on the substrate 5, as shown in FIG. 8. This electron beam exposure apparatus 100 is designed such that the element exposure regions (EF) to be exposed by the respective electron beams are adjacent two-dimensionally. A subfield (SF) constituted by the plurality of element exposure regions (EF) is exposed at once.

The subcontroller 120 instructs the deflection control circuit 115 to deflect the plurality of electron beams by the deflector 6 in a direction (X direction) perpendicular to the scanning direction (Y direction) of the X-Y stage 11 during scanning and exposure, so that after one subfield (SF1) is exposed, the next subfield (SF2) is exposed.

When the subfields are switched in this manner, the aberration with which the electron beams are reduced and projected through the reduction electron optical system 4 also changes. Hence, the subcontroller 120 instructs the LAU control circuit 112, D_STIG control circuit 113, and D_focus control circuit 114 to adjust the lens array unit LAU, dynamic stigmatic coil 8, and dynamic focus coil 7 so as to correct the changed aberration.

After the subfields are switched, a plurality of electron beams expose the corresponding element exposure regions (EF) again, thereby exposing the second subfield (SF2). In this manner, exposure of the subfields SF1 to SF6 is sequentially performed as shown in FIG. 8, thereby completing exposure of the main field (MF) constituted by the subfields SF1 to SF6 aligned in the direction (X direction) perpendicular to the scanning direction (Y direction) of the X-Y stage 11 during scanning and exposure.

After exposure of the first main field (MF1) shown in FIG. 8 is completed in this manner, the subcontroller 120 instructs the deflection control circuit 115 to sequentially deflect the plurality of electron beams toward main fields (MF2, MF3, MF4, . . . ) aligned in the scanning direction (Y direction), thus performing exposure. Hence, as shown in FIG. 8, a stripe region (STRIPE1) constituted by the main fields (MF2, MF3, MF4, . . . ) is exposed.

Subsequently, the subcontroller 120 instructs the stage drive control circuit 118 to move the X-Y stage 11 in the X direction in the stepping manner, to expose the next stripe region (STRIPE2).

Figure 9:
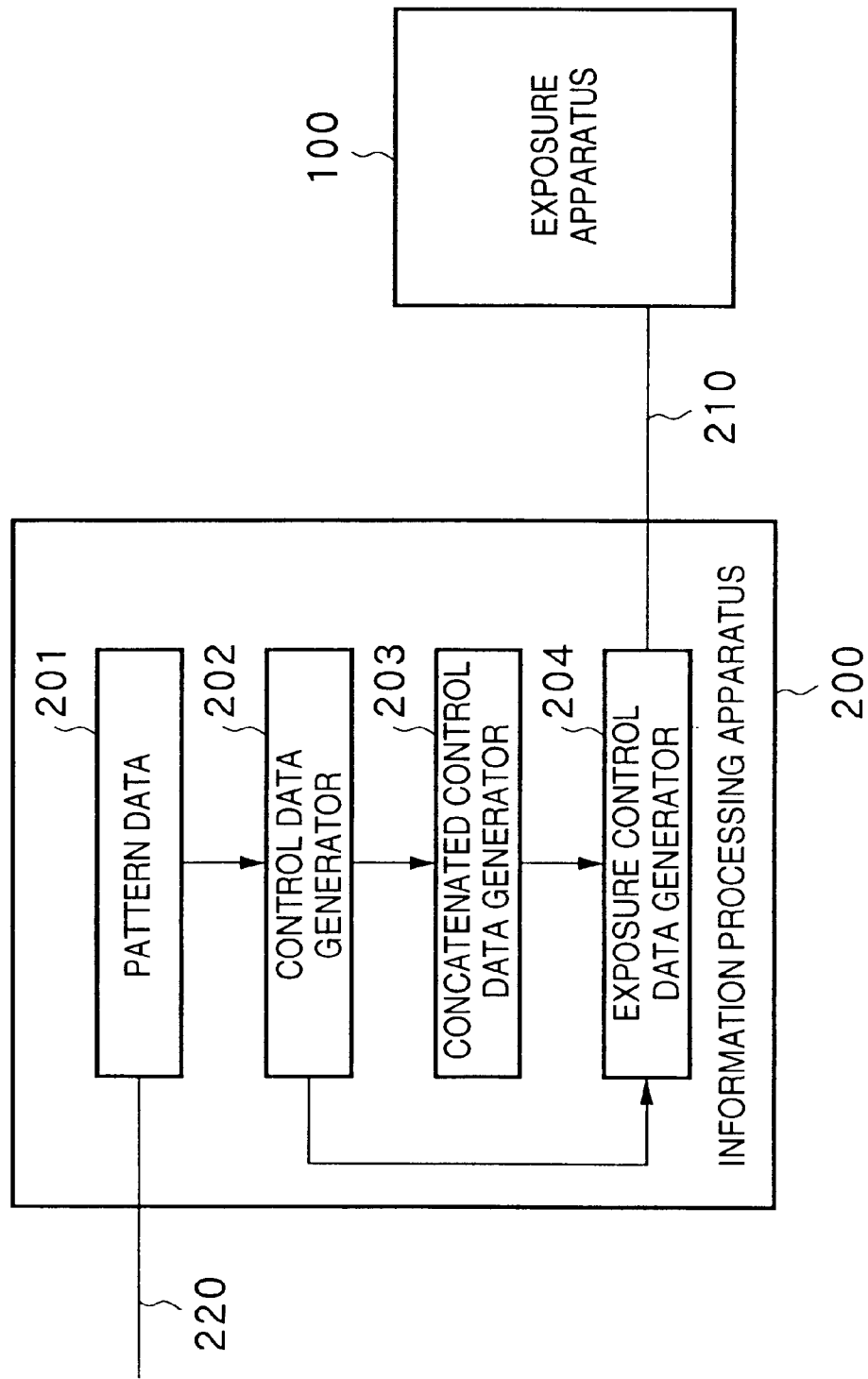
FIG. 9 is a block diagram showing the arrangement of an exposure system according to a preferable embodiment of the present invention.

FIG. 9 is a block diagram showing the arrangement of an exposure system according to a preferable embodiment of the present invention. This exposure system is obtained by connecting the electron beam exposure apparatus 100 shown in FIG. 1 and an information processing apparatus 200 with a communication cable 210. For example, the information processing apparatus 200 acquires exposure pattern data from another information processing apparatus through a communication line 220, generates compressed exposure control data matching the exposure apparatus 100 on the basis of the acquired exposure pattern data, and supplies it to the electron beam exposure apparatus 100 through the communication cable 210.

More specifically, the information processing apparatus 200 acquires the exposure pattern data from another information processing apparatus through the communication line 220, and stores it in a storage 201. The exposure pattern data may be acquired from a memory medium (e.g., a magnetic tape or disk) which stores it.

In the information processing apparatus 200, a control data generator 202 subsequently generates a plurality of control data for controlling the plurality of control elements (e.g., a plurality of blankers provided to the blanker array BA, deflector 6, dynamic focus coil 7, and the like) of the electron beam exposure apparatus 100 on the basis of the exposure pattern data.

Then, in the information processing apparatus 200, a concatenated control data generator 203 divides the plurality of control data generated by the control data generator 202 into groups each made up of at least two control data (e.g., at least two dot control data for controlling at least two blankers during a unit period) as a unit, and concatenates and then compresses the control data belonging to each group, thereby generating a plurality of compressed concatenated control data. How to generate the compressed concatenated control data will be described later.

In the information processing apparatus 200, an exposure control data generator 204 arranges the plurality of compressed concatenated control data generated by the concatenated control data generator 203 in, e.g., the order with which they are used when controlling the control elements of the electron beam exposure apparatus 100, and adds another control data if necessary, thereby generating exposure control data. Since the exposure control data is mostly made up of the plurality of compressed concatenated control data, its data size is very small. In place of performing compression during generation of the concatenated control data, a plurality of non-compressed concatenated control data may be generated and arranged to generate exposure control data. After that, the exposure control data may be compressed in units of concatenated control data.

The information processing apparatus 200 supplies the generated exposure control data to the electron beam exposure apparatus 100 through, e.g., the communication cable 210.

Figure 10:
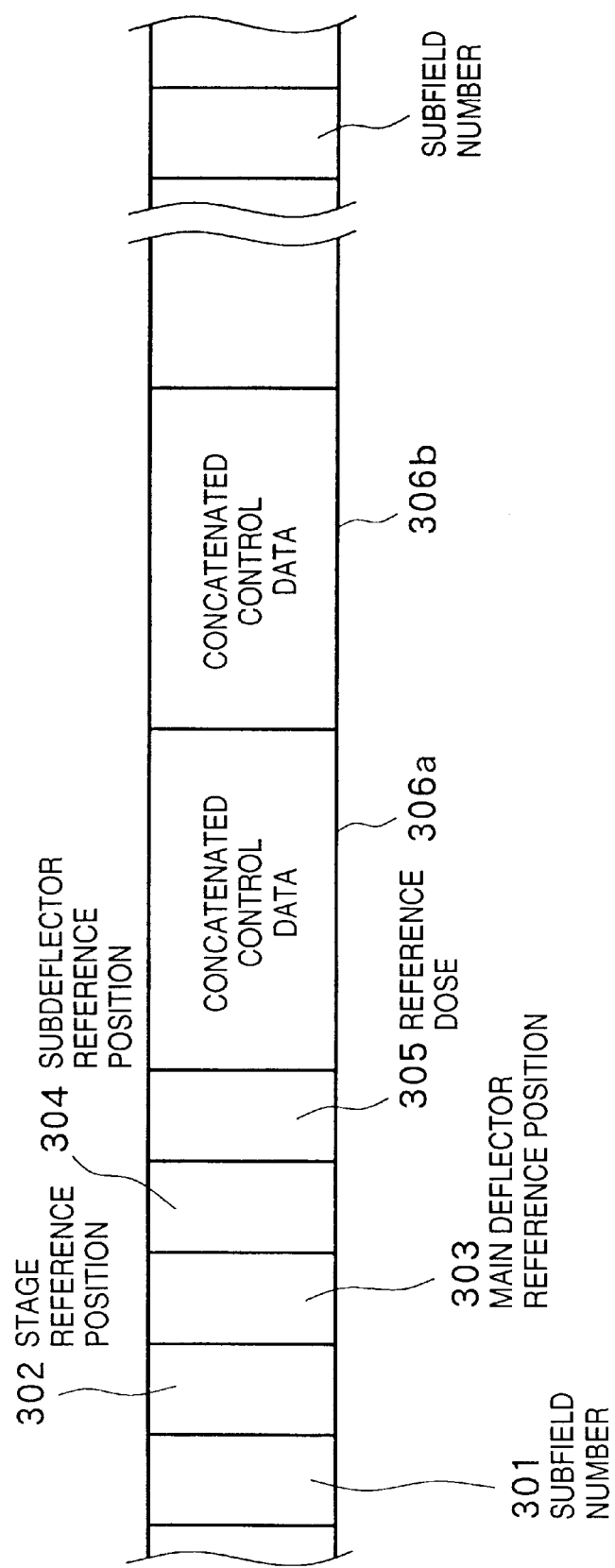
FIG. 10 is a view showing the format of exposure control data generated by an information processing apparatus.

An example of how to generate the exposure control data with the information processing apparatus 200 will be described. FIG. 10 is a view showing the format of the exposure control data generated by the information processing apparatus 200. In FIG. 10, for the sake of descriptive convenience, only one partial exposure control data for controlling exposure of one subfield (SF) is shown. Note that the whole exposure control data includes a plurality of partial exposure control data for controlling exposure of all the subfields (SF).

Partial exposure control data concerning one subfield (SF) includes a subfield number 301, stage reference position 302, main deflector reference position 303, subdeflector reference position 304, reference dose 305, and a plurality of compressed concatenated control data 306a, 306b, . . . (only two are shown).

The subfield number 301 is a number that specifies a subfield (SF). The stage reference position 302 is the reference position of the X-Y stage 11 during exposure of this subfield. The main deflector reference position 303 is the reference, on the coordinate system of the X-Y stage 11 (or the reference of the amount of deflection), for the position at which the electron beam deflected by the main deflector of the deflector 6 comes incident on the X-Y stage 11 during exposure of this subfield. The subdeflector reference position 304 is the reference, on the coordinate system of the X-Y stage 11 (or the reference of the amount of deflection), for the position at which the electron beam deflected by the subdeflector of the deflector 6 comes incident on the X-Y stage 11 during exposure of this subfield.

Each of the concatenated control data 306a, 306b, . . . is generated by dividing a plurality of control data for controlling a plurality of control elements (e.g., the plurality of blankers provided to the blanker array BA) of the electron beam exposure apparatus 100 within a predetermined unit period (e.g., a period for scanning one line of the element exposure region with an electron beam) into a plurality of groups each made up of at least two control data as a unit, and concatenating and then compressing control data belonging to the corresponding group.

According to this embodiment, each concatenated control data is generated by concatenating and compressing at least two control data each for controlling at least two control elements. A plurality of concatenated control data each generated in this manner are arranged to generate the exposure control data. Therefore, in the electron beam exposure apparatus, a plurality of control data that constitute each concatenated control data can be expanded at once, so that the expansion efficiency can be increased.

Figure 11:
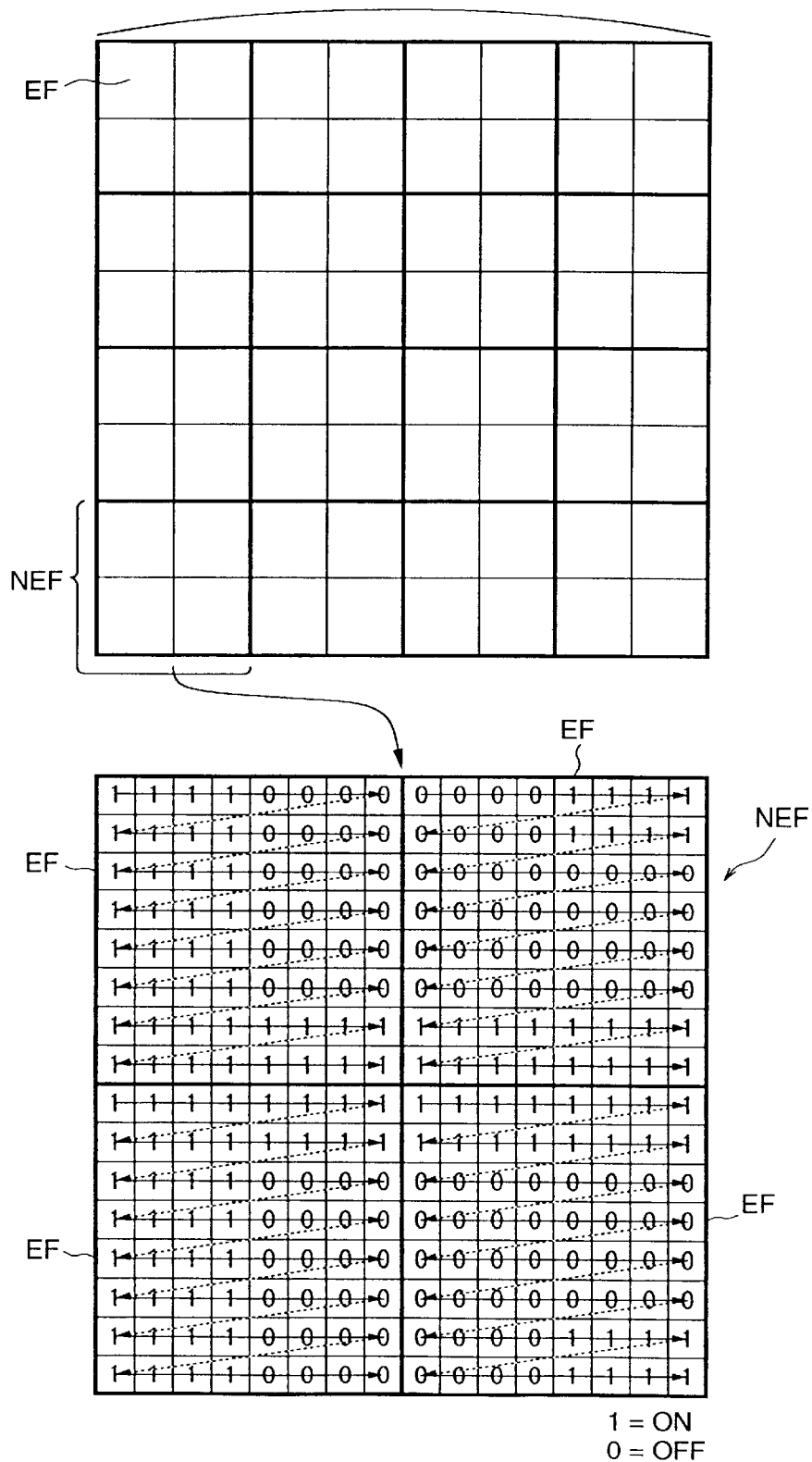
FIG. 11 shows the relationship between element exposure regions (EF) and a subfield (SF)

FIG. 11 shows the relationship between the element exposure regions (EF) and a subfield (SF). In the example shown in FIG. 11, the element exposure region (EF) is constituted by a matrix of 8×8 elements. Each element of the matrix indicates a region (position) where the electron beam deflected by the deflector 6 irradiates the substrate 5. In other words, each element exposure region (EF) constituted by the matrix of 8×8 elements is scanned by the electron beam in the order indicated by arrows in FIG. 11.

Figure 14:
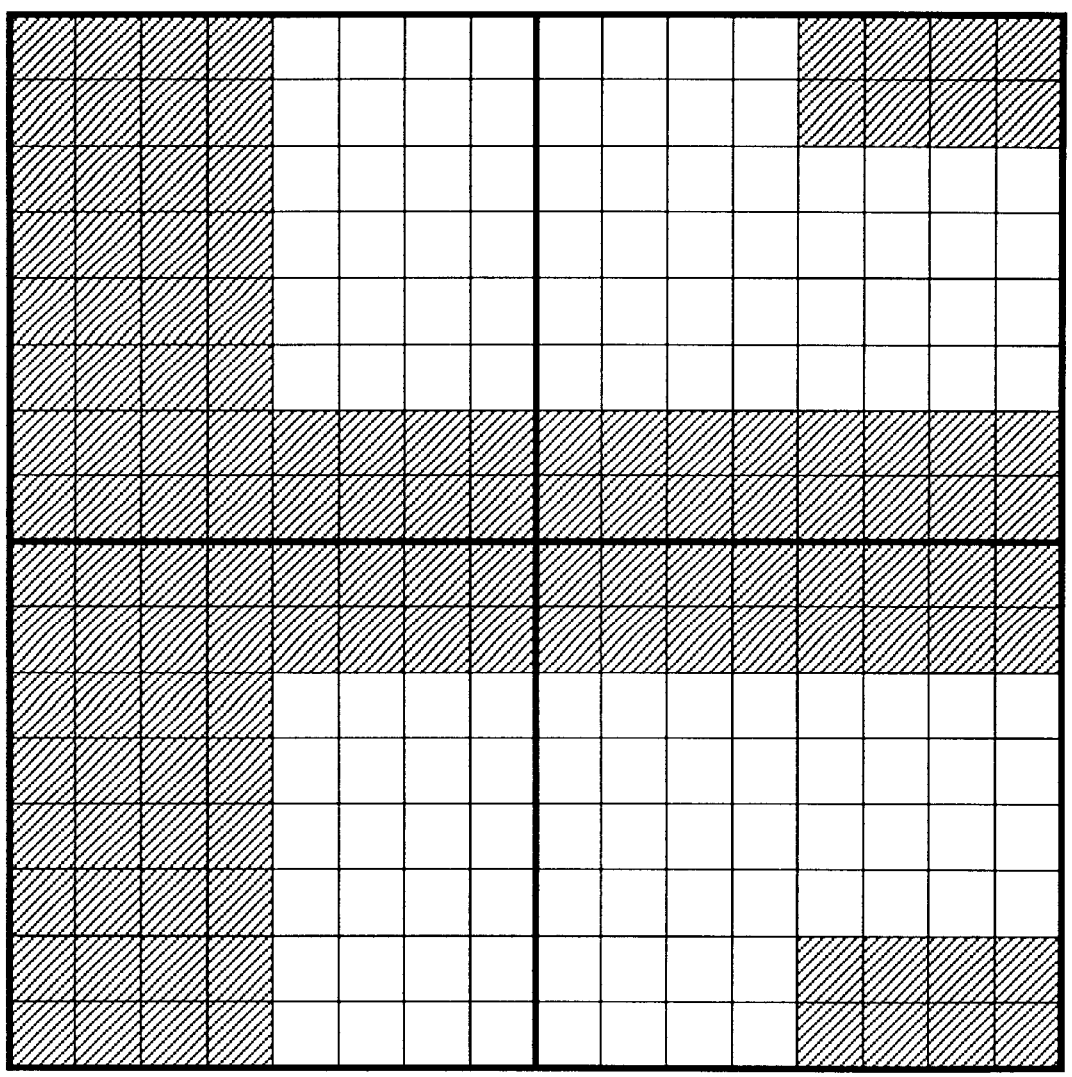
FIG. 14 shows a pattern corresponding to the dot control data shown in FIG. 11.

In FIG. 11, "1" is a region to be irradiated with the electron beam, or dot control data (blanker: OFF) indicating that this region is to be irradiated with the electron beam, and "0" is a region not to be irradiated with the electron beam, or dot control data (blanker: ON) indicating that this region is not to be irradiated with the electron beam. FIG. 14 shows a pattern corresponding to the dot control data shown in FIG. 11.

Figure 12:
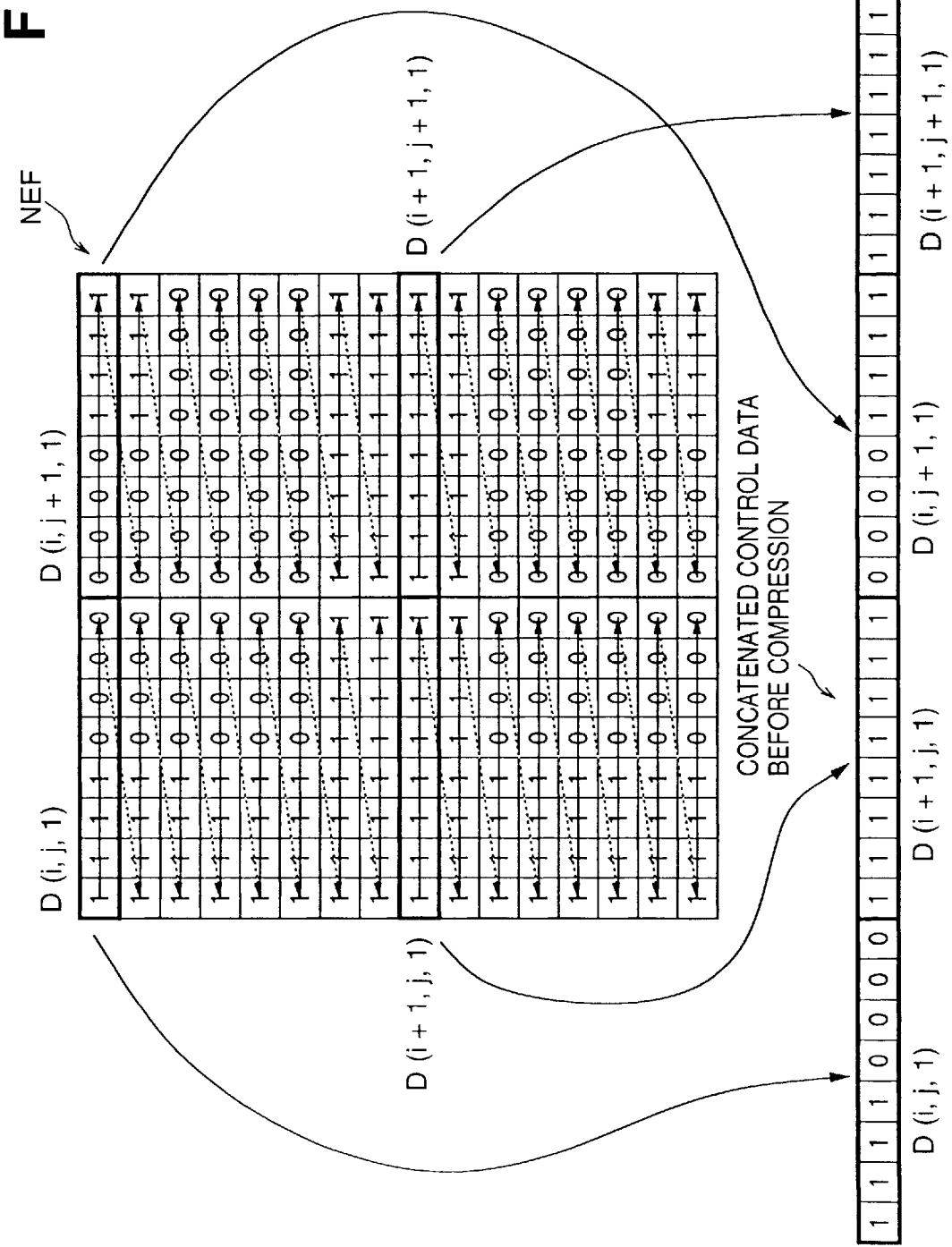
FIG. 12 shows an example of how to concatenate control data (i.e., dot control data) that control ON/OFF of an electron beam by a blanker.

FIG. 12 shows an example of how to concatenate the plurality of control data (i.e., dot control data) that control ON/OFF of the electron beam by the blanker. FIG. 12 shows an adjacent element exposure region NEF constituted by a 2×2 element exposure region (EF) and extracted from the subfield (SF). In D(i, j, k) of FIG. 12, i signifies the row position of the element exposure region in the subfield (SF), j signifies the column position of the element exposure region in the subfield (SF), and k signifies a row in the element exposure region. For example, D(i, j, 1) signifies the first row of an element exposure region specified by i and j.

In the example shown in FIG. 12, dot control data D(i, j, k), D(i+1, j, k), D(i, j+1, k), and D(i+1, j+1, k) on the same rows of four adjacent element exposure elements in the subfield (SF) (i.e., four element exposure regions in the adjacent element exposure region NEF) are generated and concatenated in series to each other. The concatenated data constituted by the four control data is compressed as a unit, thereby generating one compressed concatenated control data (306a or 306b in FIG. 10). The dot data on the same rows are time series data for controlling the blankers in the same period. In FIGS. 11 and 12, the value of i is 1, 3, 5 or 7 (the value of i+1 is 2, 4, 6, or 8), the value of j is 1, 3, 5 or 7 (the value of j+1 is 2, 4, 6, or 8), and the value of k is any one of 1 to 8.

FIG. 13 shows another example of how to concatenate the control data (i.e., dot control data) for controlling ON/OFF of the electron beam by the blanker. In the example shown in FIG. 13, dot control data D(i, j, k), D(i+1, j, k), D(i, j+1, k), and D(i+1, j+1, k) on the same rows of the four element exposure elements in the adjacent element exposure region NEF are generated and concatenated in series to each other. The concatenated data constituted by the four control data is compressed as a unit, thereby generating one compressed concatenated control data (306a or 306b in FIG. 10).

In this manner, the plurality of control data serving for control in the same unit period are concatenated and then compressed to generate each concatenated control data. The plurality of control data serving for control in the same unit period can accordingly be expanded simultaneously. Therefore, the load (e.g., a necessary memory capacity, expanding speed) on the expansion side (the electron beam exposure apparatus 100 side) can be reduced.

When the control data concerning a plurality of adjacent element exposure regions are concatenated, the compression efficiency can be improved. This is because patterns to be drawn on the adjacent element exposure regions are highly common.

Figure 15:
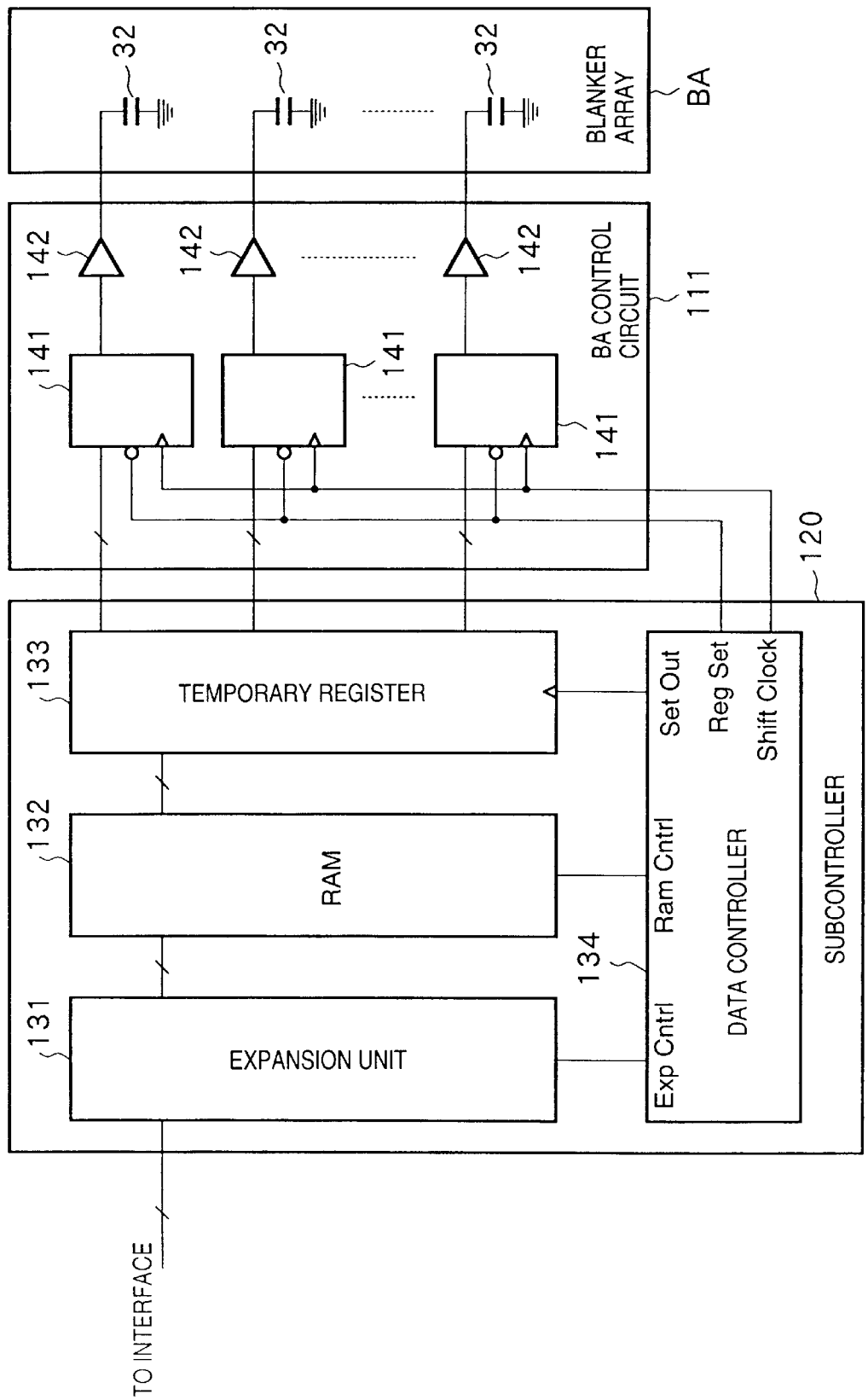
FIG. 15 is a block diagram showing part of the control system of the electron beam exposure apparatus shown in FIG. 7.

The arrangement of the electron beam exposure apparatus 100 concerning processing of the exposure control data will be described. FIG. 15 is a block diagram showing part of the control system of the electron beam exposure apparatus 100 shown in FIG. 7.

The compressed exposure control data generated by the information processing apparatus 200 is transferred to the electron beam exposure apparatus 100 through the communication cable 210, as shown in FIG. 9. The electron beam exposure apparatus 100 stores the exposure control data in the memory 121.

The subcontroller 120 reads out the compressed exposure control data from the memory (storage) 121 and controls the control circuits 111 to 116, 118, and the like on the basis of the subfield number 301, stage reference position 302, main deflector reference position 303, subdeflector reference position 304, and reference dose 305.

The subcontroller 120 includes an expansion unit 131, RAM 132, temporary register 133, and data controller 134. Note that in FIG. 15 circuits other than those for supplying the dot control data to the BA control circuit 111 are omitted.

The expansion unit 131 sequentially expands the plurality of compressed concatenated control data 306a, 306b, . . . shown in FIG. 10 on the RAM 132 in accordance with a control signal ExpCntrl supplied from the data controller 134. Accordingly, the dot control data shown in, e.g., FIG. 12 or 13, is reconstructed.

Since the electron beam exposure apparatus 100 according to this embodiment generates the concatenated control data by concatenating the dot control data of the four element exposure regions, dot control data corresponding to a unit period for the four element exposure regions are reconstructed by one expansion cycle with the expansion unit 131. However, since the electron beam exposure apparatus 100 exposes 64 element exposure regions simultaneously, 64 blankers 32 exist. Accordingly, to obtain dot control data for controlling the 64 blankers 32, 16 concatenated control data must be expanded.

The dot control data (8 bits–64) generated on the RAM 132 by expanding the 16 concatenated control data are output at once to the temporary register 133 in accordance with a control signal RamCntrl supplied from the data controller 134. The temporary register 133 fetches the dot control data and outputs them to the BA control circuit 111 in accordance with a control signal SetOut supplied from the data controller 134.

The BA control circuit 111 has shift registers 141 and buffers 142 equal in number to the number (64) of the blankers 32 of the blanker array BA. Each shift register 141 fetches an 8-bit width parallel dot control signal supplied from the temporary register 133 in accordance with a control signal RegSet supplied from the data controller 134. Each shift register 141 then converts the 8-bit width parallel dot control signal into an 8-bit serial dot control signal in accordance with a control signal ShiftClock supplied from the data controller 134, and supplies it to the corresponding blanker 32.

To suppress the capacity of the RAM 132 necessary for expansion, the unit period (i.e., the period during which the control elements are controlled in accordance with the control data generated by one expansion) must be shortened and the expanded control data must be used at once. Accordingly, with the method of generating the exposure control data by separately compressing the plurality of control data for controlling the plurality of control elements and arranging them, since the data size of each control data must be decreased, it is difficult to increase the compression efficiency. On the other hand, according to this embodiment, the plurality of control data for controlling the plurality of control elements are concatenated, and compression is performed in units of concatenated control data. Therefore, the unit of compression can be enlarged, so that the compression efficiency can be improved.

According to the embodiment described above (first embodiment), the information processing apparatus 200 generates the exposure control data including the plurality of concatenated control data generated by concatenating and compressing the plurality of dot control data for controlling the respective blankers, and the electron beam exposure apparatus 100 expands the exposure control data in units of concatenated control data. The present invention can also be applied to a method of generating exposure control data including a plurality of concatenated control data generated by concatenating and compressing different types of control data, i.e., control data for controlling different types of control elements, and expanding the exposure control data in units of concatenated control data by the electron beam exposure apparatus 100.

Figure 16:
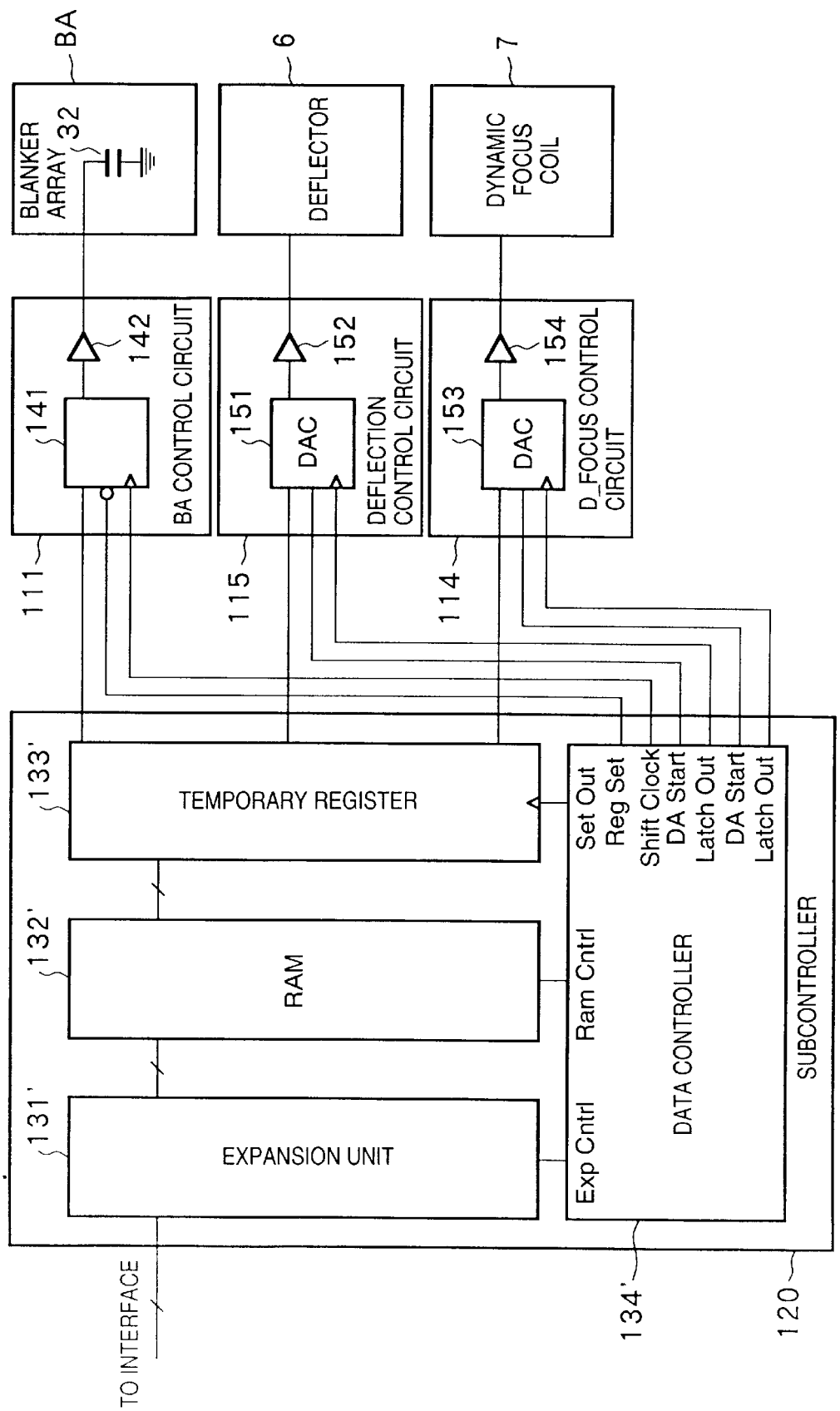
FIG. 16 is a block diagram showing another arrangement of the control system of the electron beam exposure apparatus, partly shown in FIG. 15, according to the second embodiment of the present invention.
Figure 17:
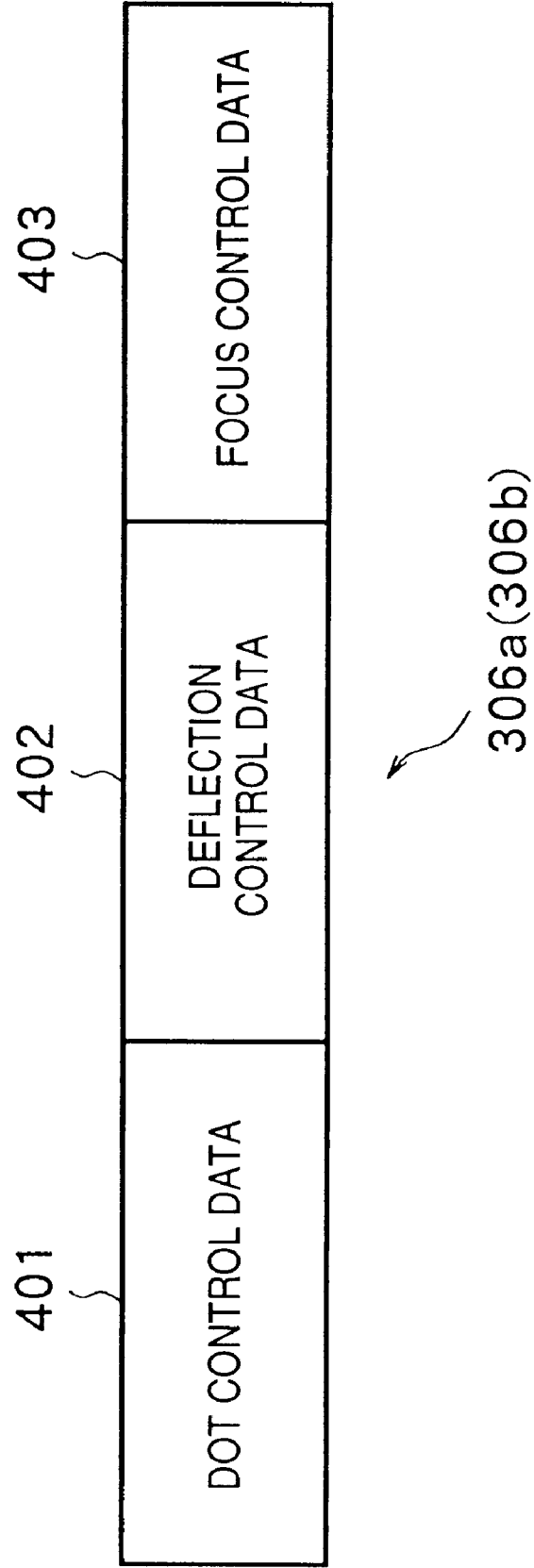
FIG. 17 is a view showing another format of each concatenated control data of the exposure control data shown in FIG. 10 according to the second embodiment of the present invention.

FIG. 16 is a block diagram showing another arrangement of the control system of the electron beam exposure apparatus 100, partly shown in FIG. 15, according to the second embodiment of the present invention. FIG. 17 is a view showing another format of each concatenated control data of the exposure control data shown in FIG. 10 according to the second embodiment of the present invention.

In the second embodiment, a plurality of dot control data 401 for controlling a plurality of blankers 32, deflection control data 402 for controlling a deflector 6, and focus control data 403 for controlling a dynamic focus coil 7 are concatenated and compressed, thereby forming one compressed concatenated control data. The dot control data 401, deflection control data 402, and focus control data 403 to be concatenated are preferably control data serving for control in the same unit period.

The exposure control data generated and compressed by an information processing apparatus 200 is transferred to an electron beam exposure apparatus 100 through a communication cable 210, as shown in FIG. 9. The electron beam exposure apparatus 100 stores the exposure control data in a memory 121.

A subcontroller 120' reads out the compressed exposure control data from the memory 121 and controls control circuits 111 to 116, 118, and the like on the basis of subfield number 301, stage reference position 302, main deflector reference position 303, subdeflector reference position 304, and reference dose 305.

The subcontroller 120' includes an expansion unit 131', RAM 132', temporary register 133', and data controller 134'.

The expansion unit 131' sequentially expands a plurality of compressed concatenated control data 306a, 306b, ... shown in FIGS. 10 and 17 on the RAM 132' in accordance with a control signal ExpCntrl supplied from the data controller 134'. Accordingly, the dot control data shown in, e.g., FIG. 12 or 13, is reconstructed, and deflection control data and focus control data are reconstructed.

Assuming that the concatenated control data is generated by concatenating and then compressing the dot control data of four element exposure regions, as in the first embodiment, dot control data corresponding to a unit period for the four element exposure regions are reconstructed by one expansion cycle with the expansion unit 131'. However, since the electron beam exposure apparatus 100 exposes 64 element exposure regions simultaneously, 64 blankers 32 exist. Accordingly, to obtain dot control data for controlling the 64 blankers 32, 16 compressed concatenated control data must be expanded. Since the deflection control data and focus control data are common to all the element exposure regions, only either one of the 16 concatenated control data may contain them.

The dot control data (8 bits×64), deflection control data, and focus control data generated on the RAM 132' are output at once to the temporary register 133' in accordance with a control signal RamCntrl supplied from the data controller 134'. The temporary register 133' fetches the dot control data, deflection control data, and focus control data in accordance with a control signal SetOut supplied from the data controller 134', and separately outputs them to the BA control circuit 111, deflection control circuit 115, and D_focus control circuit 114.

The BA control circuit 111 has shift registers 141 and buffers 142 equal in number to the number (64) of the blankers 32 of the blanker array BA. Each shift register 141 fetches an 8-bit width parallel dot control signal supplied from the temporary register 133' in accordance with a control signal RegSet supplied from the data controller 134'. Each shift register 141 then converts this parallel dot control signal into an 8-bit serial dot control signal in accordance with a control signal ShiftClock supplied from the data controller 134', and supplies it to the corresponding blanker 32 through the corresponding buffer 142.

The deflection control circuit 115 includes a D/A converter 151 and driver 152. The D/A converter 151 starts converting the deflection control data supplied from the temporary register 133' into analog data in accordance with a control signal DAStart supplied from the data controller 134', and supplies the analog deflection control data to the deflector 6 through the driver 152 in accordance with a control signal LatchOut supplied from the data controller 134'.

The D_focus control circuit 114 includes a D/A converter 153 and driver 154. The D/A converter 153 starts converting the focus control data supplied from the temporary register 133' into an analog signal in accordance with a control signal DAStart supplied from the data controller 134', and supplies the analog focus control data to the dynamic focus coil 7 through the driver 154 in accordance with a control signal LatchOut supplied from the data controller 134'.

According to this embodiment, the plurality of control data serving for control in the same unit period are concatenated and then compressed to generate each concatenated control data. The plurality of control data serving for control in the same unit period can accordingly be expanded simultaneously. Therefore, the load (e.g., a necessary memory capacity, expanding speed, and the like) on the expansion side (the electron beam exposure apparatus 100 side) can be reduced.

According to this embodiment, a plurality of control data for respectively controlling a plurality of control elements are concatenated and then compressed to generate each concatenated control data, and a plurality of concatenated control data each generated in this manner are arranged, thereby generating exposure control data. Therefore, even when the capacity of the RAM 132' is decreased, i.e., even when the unit period (the period during which the control element is controlled in accordance with the control data generated by one expansion) is shortened, the data size of the exposure control data can be reduced.

The second embodiment is described by way of a multi-electron-beam scanning apparatus for scanning a substrate with a plurality of electron beams. The second embodiment can also be applied to a single-electron-beam exposure apparatus for scanning a substrate with a single electron beam.

An embodiment of a device producing method using this electron beam exposure apparatus 100 will be described.

Figure 18:
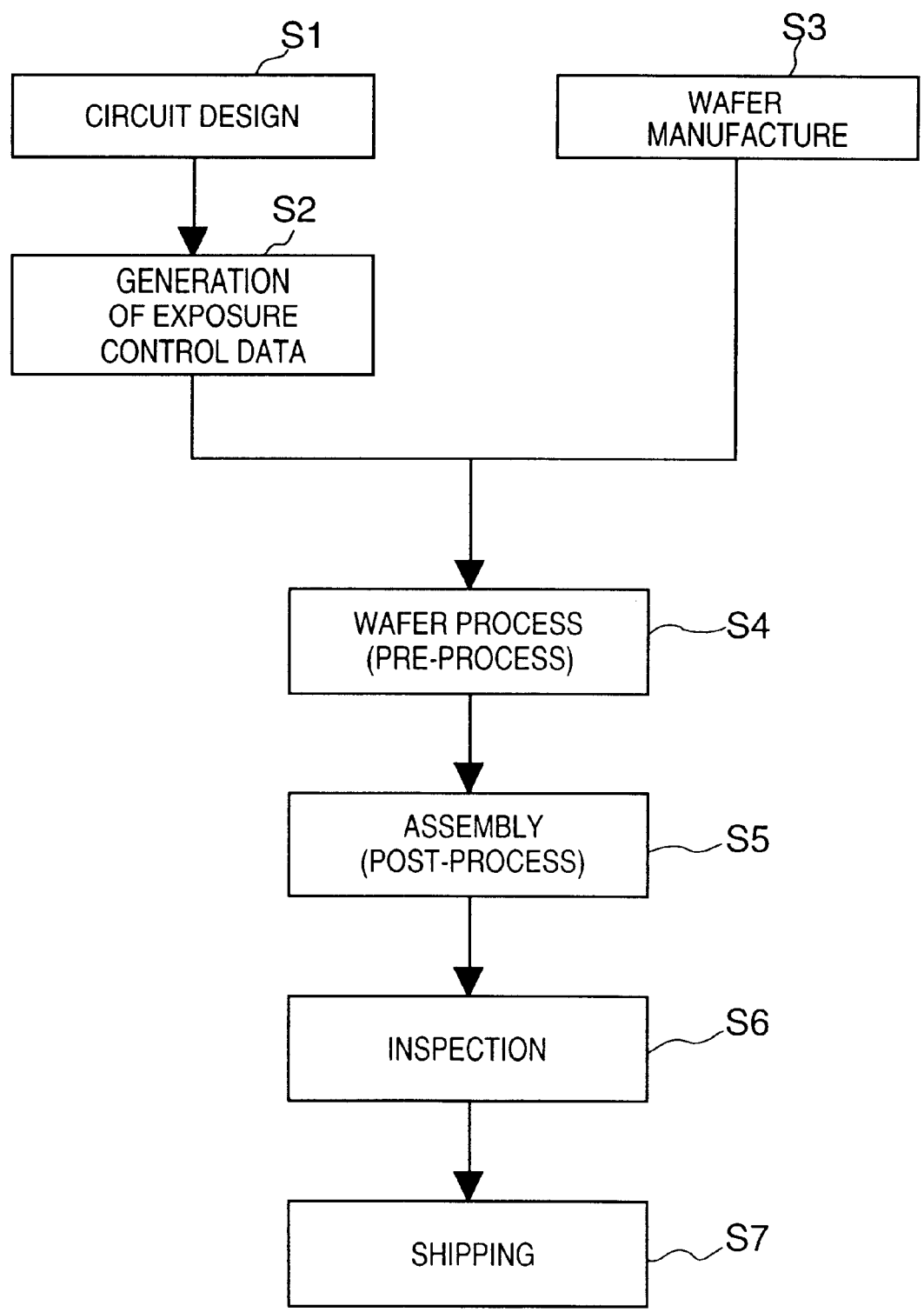
FIG. 18 shows the flow of the manufacture of a microdevice (a semiconductor chip such as an IC or LSI, a liquid crystal panel, a CCD, a thin film magnetic head, a micromachine, or the like)

FIG. 18 shows the flow of the manufacture of a microdevice (a semiconductor chip such as an IC or LSI, a liquid crystal panel, a CCD, a thin film magnetic head, a micromachine, or the like). In step 1 (circuit design), circuit design of the semiconductor device is performed. In step 2 (generation of exposure control data), the information processing apparatus 200 generates the exposure control data of the exposure apparatus on the basis of the designed circuit pattern. In step 3 (wafer manufacture), a wafer is manufactured by using a material such as silicon. Step 4 (wafer process) is called a pre-process where an actual circuit is formed on the wafer in accordance with photolithography by using the electron beam exposure apparatus 100 to which the exposure control data generated in step 2 has been input. Step 5 (assembly) is called a post-process where the wafer fabricated in step 4 is formed into semiconductor chips. Step 5 includes an assembly step (dicing, bonding), a packaging step (chip encapsulation), and the like. In step 6 (inspection), inspection such as an operation confirmation test, a durability test, and the like of the semiconductor device fabricated in step 5 is performed. The semiconductor device is completed through these steps, and is shipped (step 7).

Figure 19:
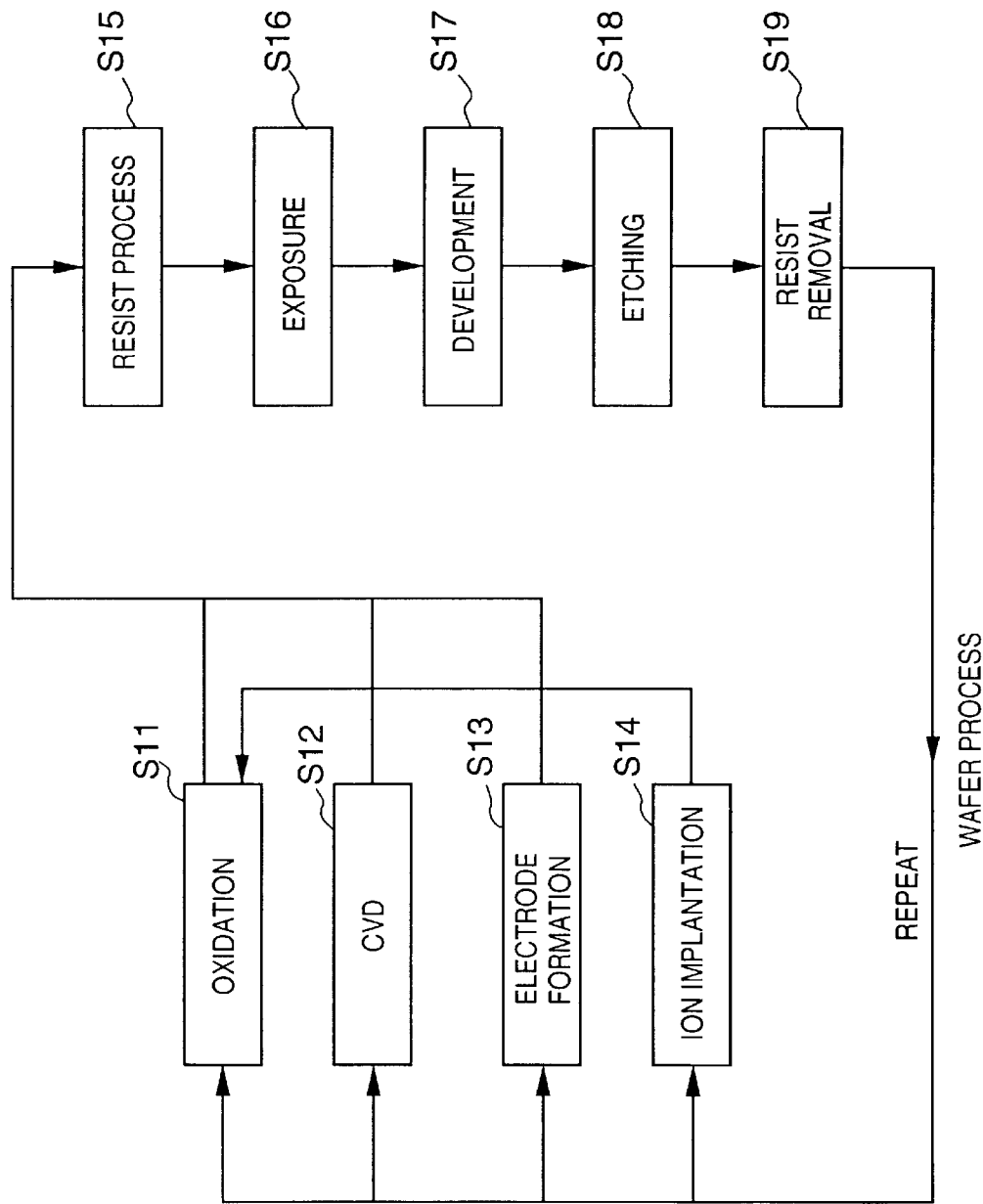
FIG. 19 shows the flow of the wafer process shown in FIG. 18 in detail.
Figure 20:
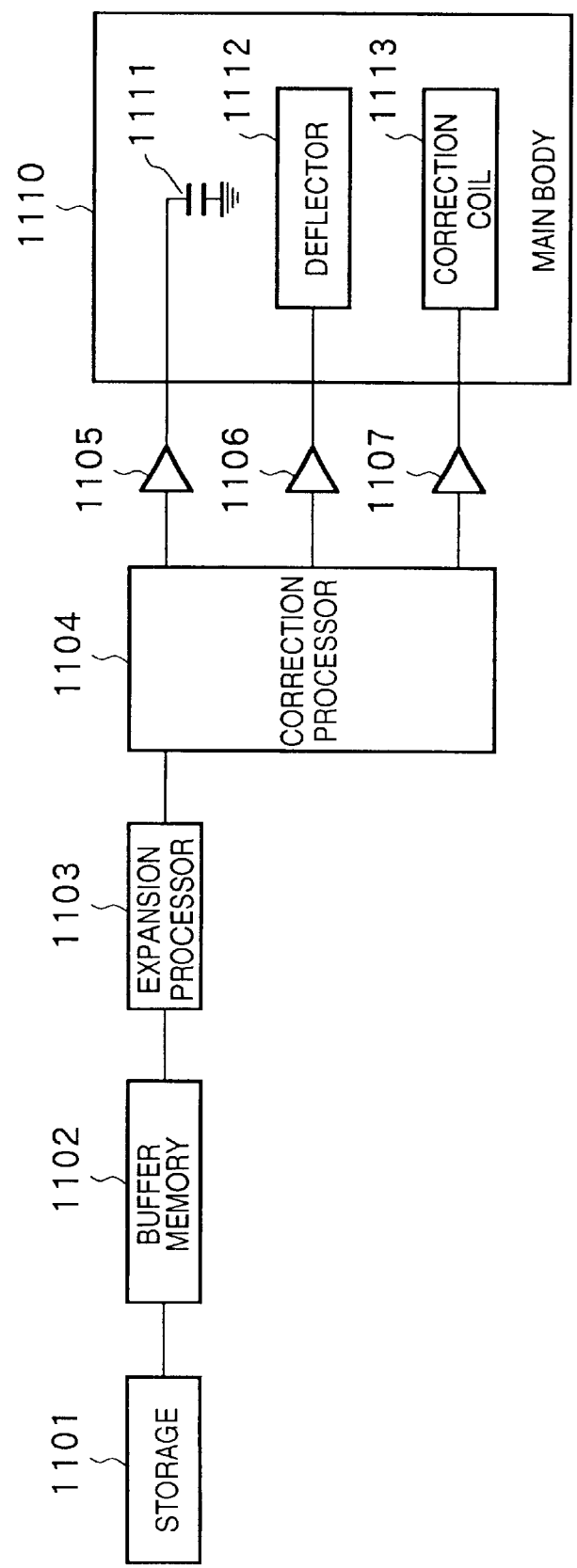
FIG. 20 is a block diagram showing the schematic arrangement of a conventional charged particle exposure apparatus.

FIG. 19 shows the flow of the wafer process shown in FIG. 18 in detail. In step 11 (oxidation), the surface of the wafer is oxidized. In step 12 (CVD), an insulating film is formed on the wafer surface. In step 13 (electrode formation), electrodes are formed on the wafer by vapor deposition. In step 14 (ion implantation), ions are implanted in the wafer. In step 15 (resist process), a photosensitive agent is applied to the wafer. In step 16 (exposure), the electron beam exposure apparatus 100 prints and exposes the circuit pattern on the wafer. In step 17 (development), the exposed wafer is developed. In step 18 (etching), a portion of the wafer other than the developed resist image is removed. In step 19 (resist removal), the resist which has become unnecessary after etching is removed. These steps are repeatedly performed to form circuit patterns on the wafer in a multiple manner.

According to the present invention, for example, the load applied to a charged particle radiation apparatus when expanding exposure control data can be reduced.

According to the present invention, for example, the data size of exposure control data to be supplied to the charged particle exposure apparatus can be reduced.

As many apparently widely different embodiments of the present invention can be made without departing from the spirit and scope thereof, it is to be understood that the invention is not limited to the specific embodiments thereof except as defined in the appended claims.

What is claimed is:

1. A charged particle exposure apparatus having a plurality of control elements for controlling operation of drawing a pattern on a substrate with a charged particle beam, comprising:

a storage for storing exposure control data including concatenated control data generated by concatenating and thereafter compressing at least two control data for respectively controlling at least two of said plurality of control elements within the same period; and a processor for reconstructing said at least two control data by expanding said concatenated control data included in said exposure control data stored in said storage, and controlling said at least two control elements in accordance with said at least two control data.

2. The apparatus according to claim 1, wherein said exposure control data includes a plurality of concatenated control data arranged in an order with which said plurality of concatenated control data are used for control.

3. The apparatus according to claim 1, wherein said at least two control elements are control elements of the same type.

4. The apparatus according to claim 1, wherein said apparatus further comprises a charged particle source for generating a plurality of charged particle beams, and said plurality of control elements include a plurality of irradiation controllers for separately controlling whether the substrate is to be irradiated with the plurality of charged particle beams.

5. The apparatus according to claim 4, wherein each of said irradiation controllers includes a blanker for controlling whether the charged particle beam is to be deflected.

6. The apparatus according to claim 4, wherein said exposure control data includes a plurality of concatenated control data, and each of said concatenated control data is generated by concatenating and compressing at least two control data for respectively controlling at least two adjacent ones of said irradiation controllers.

7. The apparatus according to claim 4, wherein said control data for controlling said irradiation controllers are time series data generated by arranging information, indicating whether the charged particle beams are to irradiate, in an order with which said information are used for control.

8. The apparatus according to claim 7, wherein said concatenated control data is generated by concatenating in series and compressing at least two of said control data serving as time series data.

9. The apparatus according to claim 7, wherein said concatenated control data is generated by concatenating in parallel and compressing at least two of said control data serving as time series data.

10. The apparatus according to claim 1, wherein said plurality of control elements include an irradiation controller for controlling whether the substrate is to be irradiated with the charged particle beam, a deflector for scanning the substrate with the charged particle beam, and a focus controller for controlling focus, and said concatenated control data is generated by concatenating and compressing at least two of control data for controlling said irradiation controller, control data for controlling said deflector, and control data for controlling said focus controller.

11. The apparatus according to claim 1, further comprising a data generator for generating said exposure control data on the basis of a pattern to be drawn on the substrate.

12. A method of controlling a charged particle exposure apparatus having a plurality of control elements for controlling operation of drawing a pattern on a substrate with a charged particle beam, the method comprising the steps of:

reading out, from a storage, exposure control data including concatenated control data generated by concatenating and thereafter compressing at least two control data for respectively controlling at least two of said plurality of control elements within the same period;

expanding said concatenated control data included in said read exposure control data, thereby reconstructing said at least two control data; and controlling said at least two control elements in accordance with said at least two control data reconstructed in the expanding step.

13. The method according to claim 12, wherein said exposure control data includes a plurality of concatenated control data arranged in an order with which said plurality of concatenated control data are used for control.

14. The method according to claim 12, wherein said at least two control elements are control elements of the same type.

15. The method according to claim 12, wherein said charged particle exposure apparatus further comprises a charged particle source for generating a plurality of charged particle beams, and said plurality of control elements include a plurality of irradiation controllers for separately controlling whether the substrate is to be irradiated with the plurality of charged particle beams.

16. The method according to claim 15, wherein each of said irradiation controllers includes a blanker for controlling whether the charged particle beam is to be deflected.

17. The method according to claim 15, wherein said exposure control data includes a plurality of concatenated control data, and each of said concatenated control data is generated by concatenating and compressing at least two control data for respectively controlling at least two adjacent ones of said irradiation controllers.

18. The method according to claim 15, wherein said control data for controlling said irradiation controllers are time series data generated by arranging information, indicating whether the charged particle beams are to irradiate, in an order with which said information are used for control.

19. The method according to claim 18, wherein said concatenated control data is generated by concatenating in series and compressing at least two of said control data serving as time series data.

20. The method according to claim 18, wherein said concatenated control data is generated by concatenating in parallel and compressing at least two of said control data serving as time series data.

21. The method according to claim 12, wherein said plurality of control elements include an irradiation controller for controlling whether the substrate is to be irradiated with the charged particle beam, a deflector for scanning the substrate with the charged particle beam, and a focus controller for controlling focus, and said concatenated control data is generated by concatenating and compressing at least two of control data for controlling said irradiation controller, control data for controlling said deflector, and control data for controlling said focus controller.

22. The method according to claim 12, further comprising the step of generating said exposure control data on the basis of a pattern to be drawn on the substrate.

23. An information processing apparatus for generating exposure control data to be supplied to a charged particle exposure apparatus having a plurality of control elements for drawing a pattern on a substrate with a charged particle beam, comprising:

a first data generator for generating concatenated control data by concatenating and compressing at least two control data for respectively controlling at least two of said plurality of control elements within the same period; and a second data generator for generating exposure control data including said concatenated control data.

24. An information processing method of generating exposure control data to be supplied to a charged particle exposure apparatus having a plurality of control elements for drawing a pattern on a substrate with a charged particle beam, comprising:

the first data generating step of generating concatenated control data by concatenating and compressing at least two control data for respectively controlling at least two of said plurality of control elements within the same period; and the second data generating step of generating exposure control data including said concatenated control data.

25. A memory medium for storing a control program which generates exposure control data to be supplied to a charged particle exposure apparatus having a plurality of control elements for drawing a pattern on a substrate with a charged particle beam, said control program including:

the first data generating step of generating concatenated control data by concatenating and compressing at least two control data for respectively controlling at least two of said plurality of control elements within the same period; and the second data generating step of generating exposure control data including said concatenated control data.

26. A device manufacturing method comprising the step of drawing a pattern on a substrate while controlling a charged particle exposure apparatus in accordance with a control method according to claim 12.

27. A device manufacturing method using, in some of steps thereof, a charged particle exposure apparatus having a plurality of control elements for controlling operation of drawing a pattern on a substrate with a charged particle beam, the method serving to perform, with said charged particle exposure apparatus, the steps of:

reading out, from a storage, exposure control data including concatenated control data generated by concatenating and thereafter compressing at least two control data for respectively controlling at least two of said plurality of control elements within the same period;

expanding said concatenated control data included in said read exposure control data, thereby reconstructing said at least two control data; and drawing a pattern on the substrate while controlling said at least two control elements and other control elements in accordance with said at least two reconstructed control data and other control data.

* * * * *

UNITED STATES PATENT AND TRADEMARK OFFICE
CERTIFICATE OF CORRECTION

PATENT NO.    : 6,483,120 B1
DATED         : November 19, 2002
INVENTOR(S)   : Yoshikiyo Yui et al.

It is certified that error appears in the above-identified patent and that said Letters Patent is hereby corrected as shown below:

Column 12,
Line 63, "(8 bits–64)" should read -- (8 bits x 64) --.

Signed and Sealed this

Thirtieth Day of September, 2003

JAMES E. ROGAN
*Director of the United States Patent and Trademark Office*